(12) United States Patent
Kirschberg et al.

(10) Patent No.: US 12,398,127 B2
(45) Date of Patent: Aug. 26, 2025

(54) THYROID HORMONE RECEPTOR BETA AGONIST COMPOUNDS

(71) Applicant: Terns Pharmaceuticals, Inc., Foster City, CA (US)

(72) Inventors: Thorsten A. Kirschberg, San Carlos, CA (US); Randall Halcomb, Foster City, CA (US); Yingzi Xu, Palo Alto, CA (US); F. Anthony Romero, Redwood City, CA (US)

(73) Assignee: Terns Pharmaceuticals, Inc., Foster City, CA (US)

( * ) Notice: Subject to any disclaimer, the term of this patent is extended or adjusted under 35 U.S.C. 154(b) by 802 days.

(21) Appl. No.: 17/642,629

(22) PCT Filed: Sep. 11, 2020

(86) PCT No.: PCT/US2020/050497
§ 371 (c)(1),
(2) Date: Mar. 11, 2022

(87) PCT Pub. No.: WO2021/050945
PCT Pub. Date: Mar. 18, 2021

(65) Prior Publication Data
US 2022/0356177 A1    Nov. 10, 2022

Related U.S. Application Data

(60) Provisional application No. 62/899,581, filed on Sep. 12, 2019.

(51) Int. Cl.
C07D 413/12     (2006.01)
A61P 5/14        (2006.01)

(52) U.S. Cl.
CPC .............. C07D 413/12 (2013.01); A61P 5/14 (2018.01)

(58) Field of Classification Search
CPC ................................ C07D 413/12; A61P 5/14
See application file for complete search history.

(56) References Cited

U.S. PATENT DOCUMENTS

| | | | |
|---|---|---|---|
| 4,197,307 A | 4/1980 | Gallay et al. | |
| 5,114,938 A | 5/1992 | Lindner et al. | |
| 6,787,652 B1 | 9/2004 | Dow et al. | |
| 7,807,674 B2 | 10/2010 | Haynes et al. | |
| 8,153,624 B2 | 4/2012 | Genin et al. | |
| 8,785,408 B2 | 7/2014 | Feinstein et al. | |
| 8,791,266 B2 | 7/2014 | Kawata et al. | |
| 10,800,767 B2 | 10/2020 | Kirschberg et al. | |
| 11,034,676 B2 | 6/2021 | Yu et al. | |
| 11,084,802 B2 | 8/2021 | Yu et al. | |
| 11,168,079 B2 | 11/2021 | Carpenter et al. | |
| 11,203,587 B2 | 12/2021 | Kirschberg et al. | |
| 11,964,964 B2 | 4/2024 | Jin et al. | |
| 2003/0078288 A1 | 4/2003 | Haning et al. | |
| 2004/0157844 A1 | 8/2004 | Dow et al. | |
| 2005/0085541 A1 | 4/2005 | Shiohara et al. | |
| 2008/0167313 A1 | 7/2008 | Dupont-Passelaigue et al. | |
| 2009/0005383 A1 | 1/2009 | Haynes et al. | |
| 2009/0247539 A1 | 10/2009 | Bell et al. | |
| 2010/0004271 A1 | 1/2010 | Garcia Collazo et al. | |
| 2010/0152166 A1 | 6/2010 | Genin et al. | |
| 2010/0286182 A1 | 11/2010 | Samuels et al. | |
| 2012/0129812 A1 | 5/2012 | Kawata et al. | |
| 2014/0275077 A1 | 9/2014 | Dandu et al. | |
| 2015/0051211 A1 | 2/2015 | Ji et al. | |
| 2015/0368205 A1 | 12/2015 | Ji et al. | |
| 2017/0050949 A1 | 2/2017 | Dandu et al. | |
| 2017/0334883 A1 | 11/2017 | Albrecht et al. | |
| 2018/0297987 A1 | 10/2018 | Coates et al. | |
| 2019/0111012 A1 | 4/2019 | Hanf | |
| 2019/0247404 A1 | 8/2019 | Namisaki et al. | |
| 2019/0321364 A1 | 10/2019 | Satyal et al. | |
| 2019/0352286 A1 | 11/2019 | Claremon et al. | |
| 2020/0009092 A1 | 1/2020 | Roberts et al. | |
| 2020/0054589 A1 | 2/2020 | Noel et al. | |
| 2020/0062742 A1 | 2/2020 | Kirschberg et al. | |
| 2020/0115362 A1 | 4/2020 | Kirschberg et al. | |
| 2020/0190064 A1 | 6/2020 | Yu et al. | |
| 2020/0354345 A1 | 11/2020 | Vandyck et al. | |
| 2020/0397798 A1 | 12/2020 | Mohan et al. | |
| 2020/0399249 A1 | 12/2020 | Yu et al. | |
| 2021/0379040 A1 | 12/2021 | Fenaux et al. | |
| 2021/0379043 A1 | 12/2021 | Fenaux et al. | |
| 2022/0135540 A1 | 5/2022 | Sweetana et al. | |
| 2022/0281849 A1 | 9/2022 | Kirschberg et al. | |
| 2022/0332707 A1 | 10/2022 | Du et al. | |
| 2022/0348561 A1 | 11/2022 | Kirschberg et al. | |
| 2023/0181583 A1 | 6/2023 | Jones et al. | |

(Continued)

FOREIGN PATENT DOCUMENTS

| | | |
|---|---|---|
| CN | 102898377 A | 1/2013 |
| CN | 105477636 A | 4/2016 |

(Continued)

OTHER PUBLICATIONS

Ashburner, et al., "Gene ontology: Tool for the unification of biology," Nature Genetics, 25(1): 25-9 (2000).

(Continued)

*Primary Examiner* — Sun Jae Yoo

(74) *Attorney, Agent, or Firm* — Cooley LLP

(57) ABSTRACT

Provided herein are compounds, preferably thyroid hormone receptor beta (THR beta) agonist compounds, compositions thereof, and methods of their preparation, and methods of agonizing THR beta and methods for treating disorders mediated by THR beta.

19 Claims, No Drawings

(56) References Cited

U.S. PATENT DOCUMENTS

| | | |
|---|---|---|
| 2023/0241071 A1 | 8/2023 | Fenaux et al. |
| 2023/0278988 A1 | 9/2023 | Yu et al. |
| 2024/0000765 A1 | 1/2024 | Fenaux et al. |
| 2024/0059682 A1 | 2/2024 | Kirschberg et al. |
| 2024/0156826 A1 | 5/2024 | Taub |
| 2024/0239761 A1 | 7/2024 | Zhang et al. |
| 2024/0293416 A1 | 9/2024 | Jones et al. |
| 2024/0316025 A1 | 9/2024 | Fenaux et al. |
| 2024/0360106 A1 | 10/2024 | Jin et al. |

FOREIGN PATENT DOCUMENTS

| | | |
|---|---|---|
| CN | 110167557 A | 8/2019 |
| CN | 111320609 A | 6/2020 |
| CN | 111484481 A | 8/2020 |
| CN | 111909137 A | 11/2020 |
| CN | 114430743 A | 5/2022 |
| CN | 114437034 A | 5/2022 |
| EP | 1471049 A1 | 10/2004 |
| EP | 3437659 A1 | 2/2019 |
| EP | 3807267 A1 | 4/2021 |
| JP | H02225483 A | 9/1990 |
| JP | 2001114768 A | 4/2001 |
| JP | 2007512314 A | 5/2007 |
| JP | 2009500305 A | 1/2009 |
| JP | 2011528007 A | 11/2011 |
| JP | 2015500212 A | 1/2015 |
| RU | 2668960 C2 | 10/2018 |
| WO | WO-0198256 A1 | 12/2001 |
| WO | WO-03064369 A1 | 8/2003 |
| WO | WO-03094845 A2 | 11/2003 |
| WO | WO-2007003419 A1 | 1/2007 |
| WO | WO-2007009913 A1 | 1/2007 |
| WO | WO-2007128492 A1 | 11/2007 |
| WO | WO-2007134864 A1 | 11/2007 |
| WO | WO-2009012125 A1 | 1/2009 |
| WO | WO-2009037172 A1 | 3/2009 |
| WO | WO-2010006962 A1 | 1/2010 |
| WO | WO-2010122980 A1 | 10/2010 |
| WO | WO-2011038207 A1 | 3/2011 |
| WO | WO-2014043706 A1 | 3/2014 |
| WO | WO-2017167935 A1 | 10/2017 |
| WO | WO-2017170434 A1 | 10/2017 |
| WO | WO-2018027892 A1 | 2/2018 |
| WO | WO-2018028517 A1 | 2/2018 |
| WO | WO-2018073154 A1 | 4/2018 |
| WO | WO-2018075650 A1 | 4/2018 |
| WO | WO-2018103624 A1 | 6/2018 |
| WO | WO-2018153933 A1 | 8/2018 |
| WO | WO-2018167103 A1 | 9/2018 |
| WO | WO-2018170173 A1 | 9/2018 |
| WO | WO-2018193006 A1 | 10/2018 |
| WO | WO-2018193007 A1 | 10/2018 |
| WO | WO-2018208707 A1 | 11/2018 |
| WO | WO-2019023245 A1 | 1/2019 |
| WO | WO-2019038456 A1 | 2/2019 |
| WO | WO-2019053233 A1 | 3/2019 |
| WO | WO-2019053235 A1 | 3/2019 |
| WO | WO-2019094777 A1 | 5/2019 |
| WO | WO-2019144835 A1 | 8/2019 |
| WO | WO-2019240938 A1 | 12/2019 |
| WO | WO-2020041741 A1 | 2/2020 |
| WO | WO-2020042114 A1 | 3/2020 |
| WO | WO-2020061086 A2 | 3/2020 |
| WO | WO-2020061114 A1 | 3/2020 |
| WO | WO-2020073974 A1 | 4/2020 |
| WO | WO-2020077123 A1 | 4/2020 |
| WO | WO-2020123827 A1 | 6/2020 |
| WO | WO-2020131578 A2 | 6/2020 |
| WO | WO-2020169069 A1 | 8/2020 |
| WO | WO-2020227549 A1 | 11/2020 |
| WO | WO-2020239076 A1 | 12/2020 |
| WO | WO-2021014350 A1 | 1/2021 |
| WO | WO-2021041237 A1 | 3/2021 |
| WO | WO-2021050945 A1 | 3/2021 |
| WO | WO-2021121210 A1 | 6/2021 |
| WO | WO-2021231644 A1 | 11/2021 |
| WO | WO-2021231646 A1 | 11/2021 |
| WO | WO-2022152770 A1 | 7/2022 |
| WO | WO-2022187403 A1 | 9/2022 |
| WO | WO-2023083288 A1 | 5/2023 |
| WO | WO-2023086561 A1 | 5/2023 |
| WO | WO-2023220404 A1 | 11/2023 |

OTHER PUBLICATIONS

Bashir, M., et al., "Liver Volume Reduction in Resmetirom Treated Non-Cirrhotic and Cirrhotic NASH Patients," Hepatology, Oct. 2021, vol. 74, No. 1(Suppl), pp. 1142A-1143A.

Basnak, I. et al. (1975). "Synthesis of 5-cyclopropyl-6-azauracil," Collection of Czechoslovak Chemical Communications, 40(4):1038-1042.

Baxter, J. D. et al., "Thyroid hormone mimetics: potential applications in atherosclerosis, obesity and type 2 diabetes," Nature Reviews Drug Discovery, vol. 8, No. 4, pp. 308-320 (Apr. 2009).

Belikov, V. G., Pharmaceutical Chemistry, Chapter 2.6, "Relationship between the chemical structure, the properties of substances and their effects on the body", Medpress Inform, Moscow, 2007, pp. 27-29 (with English translation).

Berry, M. J, et al., "Thyroid hormone regulates type I deiodinase messenger RNA in rat liver," Molecular Endocrinology, 1990, 4:743-748.

Brecher, J. (Jan. 2006). "Graphical Representation of Stereochemical Configuration (IUPAC Recommendations 2006)," Pure and Appl. Chem. 78(10):1897-1959.

Chen, H.C. et al. (Nov. 13-16, 2020). MET409, an Optimized Sustained FXR Agonist, Was Safe and Well-Tolerated in a 14-Day Phase 1 Study in Healthy Subjects, Metacrine, 1 page, Poster presented at Poster presentation at EASL—The International Liver Congress, Apr. 2019, Vienna, Austria.

Chung, D et al. (2020)."Pharmacokinetics Of Two Oral Formulations Of Liver-Directed, Nonsteroidal Farnesoid XReceptor Agonist Tern-101 In Healthy Volunteers," Terns Pharmaceutical, Inc., 1 page, Poster presented at Paris NASH Meeting, Oct. 22-23, 2020, Paris, France.

Dennis, A., et al., "Correlations Between MRI Biomarkers PDFF and cT1 with Histopathological Features on Non-Alcoholic Steatohepatitis," Frontiers in Endocrinology, Jan. 2021, vol. 11, Article 575843, 10 pages.

Dermer, G.B., "Another Anniversary for the War on Cancer," Bio/Technology, 12:320, 1 page (Mar. 1994).

Dufour, J.-F. et al., "Combination Therapy For Non-Alcoholic Steatohepatitis: Rationale, Opportunities And Challenges,"Gut, 69(10):1877-1884 (2020).

Dunkel, P. et al., "Semicarbazide-sensitive amine oxidase/vascular adhesion protein-1: a patent survey," Expert Opinion on Therapeutic Patents, Jun. 2011, vol. 21, No. 9, pp. 1453-1471, doi: 10.1517/13543776.2011.594040.

Erion, M.D., "Targeting thyroid hormone receptor-β agonists to the liver reduces cholesterol and triglycerides and improves the therapeutic index," PNAS USA 2007, 104(39), 15490-15495.

Extended European Search Report and Search Opinion, dated Apr. 2, 2024, for European Patent Application No. 21803928.7, 11 pages.

Extended European Search Report and Search Opinion, dated Dec. 23, 2024, for European Patent Application No. 22764006.7, 10 pages.

Extended European Search Report and Search Opinion, mailed Aug. 17, 2023, for European Patent Application No. 20863146.5, 7 pages.

Extended European Search Report and Search Opinion, mailed Jul. 6, 2022, for European Application No. 19896475.1 (8 total pages).

Extended European Search Report and Search Opinion, mailed Mar. 30, 2023, for European Application No. 20856291.8 (8 total pages).

Extended European Search Report and Search Opinion, dated May 18, 2022, for European Patent Application No. 19870196.3 (5 total pages).

Extended Search Report and Search Opinion, mailed Mar. 22, 2022, for European Patent Application No. 19852050.4 (7 total pages).

(56) References Cited

OTHER PUBLICATIONS

Fiorucci, S. et al., "Future trends in the treatment of non-alcoholic steatopehatits," Pharmacological Research, Jul. 2018, vol. 134, pp. 289-298, doi: 10.1016/J.PHRS.2018.07.014.
Freshney, R. I., et al., "Culture of Animal Cells," A Manual of Basic Technique, 1983, Alan R. Liss, Inc., New York, p. 4 and pp. 129-133 (9 total pages).
Gallup. Americans' Average Weight Holds Steady in 2020, Jan. 4, 2021, Retrieved from the Internet on Sep. 27, 2023, https://news.gallup.com/poll/328241/americans-average-weight-holds-steady-2020.aspx, 9 pages.
Gene Ontology Consortium, Creating the Gene Ontology Resource: Design and Implementation. Genome Research 11: 1425-1433 (2001).
Grover et al., "Effects of the thyroid hormone receptor Agonist GC-1 on metabolic rate and cholesterol in rats and primates: selective actions relative to 3,5,3'-triiodo-L-thyronine," Endocrinology, vol. 145, No. 4, pp. 1656-1661 (Apr. 2004).
Han, C.Y., "Update on FXR Biology: Promising Therapeutic Target?", International Journal of Molecular Sciences, Int. J. Mol. Sci., 19, 2069, 25 pages (Jul. 2018).
Hansen, H. H., et al., "Human translatability of the GAN diet-induced obese mouse model of non-alcoholic steatohepatitis," BMC Gastroenterology 2020, 20:210, pp. 1-12.
Harrison, S. A., et al., "A Phase 3, Randomized, Controlled Trial of Resmetirom in NASH with Liver Fibrosis," The New England Journal of Medicine, Feb. 8, 2024, vol. 390, No. 6, pp. 497-509.
Harrison, S. A., et al., "Resmetirom for nonalcoholic fatty liver disease: a randomized, double-blind, placebo-controlled phase 3 trial," Nature Medicine, Nov. 2023, vol. 29, 2919-2928, including additional material, 19 pages, DOI: 10.1038/s41591-023-02603-1.
Hennessey, J. V., et al., "The emergence of levothyroxine as a treatment for hypothyroidism," Endocrine, 2017, 55: 6-18, DOI: 10.1007/s12020-016-1199-8.
Hill, S. R. Jr., et al., "The Metabolic Effects of the Acetic and Propionic Acid Analogs of Thyroxine and Triiodothyronine," J Clin. Invest. 1960, (39):523-533.
Ichiki, T., et al., "Thyroid Hormone and Vascular Remodeling," Journal of Atherosclerosis and Thrombosis, 2016, vol. 23, No. 3, pp. 266-275.
International Preliminary Report on Patentability, issued Jan. 19, 2010, for PCT Application No. PCT/US2008/069719, filed Jul. 11, 2008, 7 pages.
International Preliminary Report on Patentability, mailed Apr. 22, 2021, for International Application No. PCT/US2019/055689, 9 pages.
International Preliminary Report on Patentability, mailed Jun. 24, 2021, for International Application No. PCT/US2019/066013, 6 pages.
International Preliminary Report on Patentability, mailed Mar. 11, 2021, for International Application No. PCT/US2019/047968 (7 total pages).
International Preliminary Report on Patentability, mailed Mar. 11, 2021, for PCT Application No. PCT/CN2018/103349, filed Aug. 30, 2018, 7 pages.
International Preliminary Report on Patentability, mailed Mar. 24, 2022, for International Application No. PCT/US2020/050497 (7 total pages).
International Preliminary Report on Patentability, mailed Mar. 3, 2022, for International Application No. PCT/US2020/047467 (9 total pages).
International Preliminary Report on Patentability, mailed May 23, 2024, for International Application No. PCT/CN2022/131297, 7 pages.
International Preliminary Report on Patentability, mailed May 23, 2024, for International Application No. PCT/US2022/049690, 12 pages.
International Preliminary Report on Patentability, mailed Nov. 24, 2022, for International Application No. PCT/US2021/032085 (12 total pages).
International Preliminary Report on Patentability, mailed Nov. 28, 2024, for International Application No. PCT/US2023/022093, 6 pages.
International Preliminary Report on Patentability, mailed Sep. 14, 2023, for International Application No. PCT/US2022/018575, 18 pages.
International Search Report and Written Opinion, mailed Aug. 2, 2023, for International Application No. PCT/US2023/022093, 8 pages.
International Search Report and Written Opinion, mailed Dec. 8, 2020, for International Application No. PCT/US2020/050497 (9 total pages).
International Search Report and Written Opinion mailed Feb. 5, 2021, for International Application No. PCT/US2020/059522, filed Nov. 6, 2020, 9 pages.
International Search Report and Written Opinion, mailed Feb. 10, 2023, for International Application No. PCT/CN2022/131297, 10 Pages.
International Search Report and Written Opinion, mailed Feb. 28, 2020, for International Application No. PCT/US2019/066013, 8 pages.
International Search Report and Written Opinion, mailed Jan. 15, 2021, for International Application No. PCT/US2020/047467, 12 pages.
International Search Report and Written Opinion, mailed Jan. 23, 2020, for International Application No. PCT/US2019/055689, 12 Pages.
International Search Report and Written Opinion, mailed Jun. 5, 2019, for International Application No. PCT/CN2018/103349 (9 total pages).
International Search Report and Written Opinion, mailed Mar. 16, 2023, for International Application No. PCT/US2022/049690 (21 total pages).
International Search Report and Written Opinion, mailed May 23, 2022, for International Application No. PCT/US2022/018575 (21 total pages).
International Search Report and Written Opinion, mailed Nov. 21, 2019, for International Application No. PCT/US19/47968, 9 pages.
International Search Report and Written Opinion, mailed Nov. 6, 2008, for International Application No. PCT/US2008/069719, 9 pages.
International Search Report and Written Opinion, mailed Sep. 30, 2021, for International Application No. PCT/US2021/032085 (17 total pages).
Invitation to Pay Additional Fees, and, Where Applicable, Protest Fee, dated Jul. 6, 2021, for International Application No. PCT/US2021/032083 (3 total pages).
Invitation to Pay Additional Fees, dated Nov. 21, 2019, for International Application No. PCT/US2019/055689, 2 pages.
Invitation to Pay Additional Fees, mailed Jul. 6, 2021, for PCT Application No. PCT/US2021/032085, 3 pages.
Invitation to Pay Additional Fees, mailed Oct. 4, 2020, for International Application No. PCT/US2020/047467, 2 pages.
Jones, C. et al., "Combination of TERN-101, A Farnesoid X Receptor Agonist, and TERN-501, A Selective Agonist of Thyroid Hormone Receptor Beta, Reduces Activation of Inflammatory and Fibrotic Gene Pathways in a Mouse Model of Non-Alcoholic Steatohepatilis," Terns Pharmaceuticals Inc., Poster #0517, 1 page, Poster presented at AASLD The Liver Meeting, Nov. 13-16, 2020.
Jones, C., et al., EASL, Aug. 28, 2020, Single doses of TERN-201, a novel selective semicarbazide-sensitive amine oxidase (SSAO) inhibitor, are safe, well-tolerated, and result in sustained reduction of SSAO activity in healthy participants, Poster, 1 page.
Jones, C., et al., Single doses of the THR-β agonist TERN-501 are well tolerated and result in dose-dependent changes in LDL cholesterol and sex hormone binding globulin in a first-in-human clinical trial, AASLD, Nov. 12-15, 2021, Poster No. 1889, 1 page.
Kawamata, Y. et al., "A G Protein-Coupled Receptor Responsive To Bile Acids," The Journal of Biological Chemistry, vol. 278, No. 11, pp. 9435-9440 (Mar. 14, 2003).
Kelly M. J., et al., "Discovery of 2-[3,5-Dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL3196), a Highly Selec-

(56) References Cited

OTHER PUBLICATIONS tive Thyroid Hormone Receptor beta Agonist in Clinical Trials for the Treatment of Dyslipidemia," Journal of Medicinal Chemistry, vol. 57, No. 10, pp. 3912-3923, DOI:10.1021/jm4019299 (Apr. 2014).

Kim D., et al., "Critical Roles of the Histone Methyltransferase MLL4/KMT2D in Murine Hepatic Steatosis Directed by ABL1 and PPARgamma2," Cell Reports, 2016, vol. 17(6), pp. 1671-1682, DOI: 10.1016/j.celrep.2016.10.023.

Kirschberg, T., et al., EASL, Aug. 29, 2020, "TERN-501, a potent and selective agonist of thyroid hormone receptor beta, strongly reduces histological features and biomarkers of non-alcoholic steatohepatitis associated pathology in rodent models," poster, 1 page.

Kirschberg, T., et al., "TERN-501, a potent and selective agonist of thyroid hormone receptor beta, strongly reduces histological features and biomarkers of non-alcoholic steatohepatitis associated pathology in rodent models," Journal of Hepatology 2020, vol. 73, S653-S915, page S684, SAT066.

Klein, I. et al. (Oct. 9, 2007). "Cardiovascular Involvement in General Medical Conditions, Thyroid Disease and the Heart," Circulation 116(15):1725-1735.

Kleiner, D. E., et al., "Design and validation of a histological scoring system for nonalcoholic fatty liver disease," Hepatology, Jun. 2005, 41(6):1313-1321.

Klucher, K., et al., EASL, Aug. 29, 2020, Anti-inflammatory and anti-fibrotic activity of TERN-201, a semicarbazide-sensitive amine oxidase inhibitor, in a rat choline-deficient high-fat diet non-alcoholic steatohepatitis model, Poster, 1 page.

Kogler, M. (Mar. 2012). "Synthesis and Evaluation of 6-aza-2'-deoxyuridine Monophosphate Analogs as Inhibitors of Thymidylate Synthases, and as Substrates or Inhibitors of Thymidine Monophosphate Kinase in *Mycobacterium tuberculosis*," Chemistry and Biodiversity, 9(3):536-556.

Kowalik et al., "Thyroid Hormones, Thyromimetics and Their Metabolites in the Treatment of Liver Disease," Frontiers in Endocrinology, vol. 9, Article 382, pp. 1-11 (Jul. 2018).

Krchnak, V. et al., "Novel Pyrimidine Derivatives, Reactions and Ultraviolet Spectra," Collect. Czech. Chem. Commun. 1975, 40(5):1038-1042.

Kremoser, C., "FXR Agonists For NASH: How Are They Different And What Difference Do They Make?", Journal of Hepatology 2021, vol. 75, pp. 12-15.

Liver Meeting® Digital Experience 2020, Oct. 14, 2020, 3 pages, https://www.ternspharma.com/10-14-20-terns-to-present-positive-data-on-single-agent-and-combo-nash-at-liver-meeting-exp-2020).

Loomba, R., et al., "Nonalcoholic fatty liver disease progression rates to cirrhosis and progression of cirrhosis to decompensation and mortality: a real world analysis of Medicare data," Alimentary Pharmacology and Therapeutics, 2020, 51:1149-59.

Loomba, R., et al., Relationship of Non-Invasive Measures with Histological Response in Patients with NonAlcoholic Steatohepatitis and Fibrosis: 52-Week Data from the Phase 3 Maestro-NASH Trial, Hepatology, 2023, 78 (Suppl 1):S155-S159, Abstract 149.

Nelson, C. H., et al., Multiple Doses of Thyroid Hormone Receptor-Beta Agonist TERN-501 were Well-Tolerated and Resulted in Significant Dose-Dependent Changes in Serum Lipids and Sex Hormone Binding Globulin in a First-in-Human Clinical Study, EASL, Presentation, Abstract No. OS123, Jun. 25, 2022, 18:15-18-30, 17 pages.

Nelson, C. H., et al., Thyroid Hormone Beta Receptor Agonist Tern-501 Demonstrates Dose- And Exposure-Dependent Increases In Sex Hormone Binding Globulin With Associated Decreases In Atherogenic Lipids In Healthy Subjects, AASLD The Liver Meeting, Nov. 4-8, 2022, poster, 1 page.

Nelson, R. H., "Hyperlipidemia as a risk factor for cardiovascular disease," Primary Care, Mar. 2013, 40(1):195-211.

Noureddin, M., et al., "Head-to-Head Comparison of Fast, Mast, MEFIB and cT1 in Identifying At-Risk NASH Patients in a Low-Prevalence Population," Hepatology, 2023, 78(Supplement 1):S1-S2154, pp. S806-S810, Abstract 2050-A.

Noureddin, M., et al., "5000 | Topline Results from a 12-Week Phase 2a Trial (Duet) Evaluating Tern-501, A Highly Selective Thyroid Hormone Receptor (THR) Beta Agonist, Either as Monotherapy or in Combination with TERN-101, A Nonsteroidal Farnesoid X Receptor (FXR) Agonist, Demonstrated Significant Reductions in MR-Based Liver Fat Content and Fibroinflammation in Patients with Presumed MASH," Hepatology 2024, 79:E33-E85, p. E33.

Obach, R. S. et al., "The Prediction of Human Pharmacokinetic Parameters from Preclinical and In Vitro Metabolism Data," The Journal of Pharmacology and Experimental Therapeutics, vol. 283, No. 1, pp. 46-58 (1997).

Pagadala, M. R, et al., "Prevalence of hypothyroidism in nonalcoholic fatty liver disease," Digestive Diseases and Sciences, 2012, 57:528-34.

Pubchem (Jan. 12, 2016). "4-(1,2,4-Benzotriazin-3-Yloxy)-N-Methylaniline," CID: 103204817, 7 pages.

Reagan-Shaw, S., et al., "Dose translation from animal to human studies revisited," The FASEB Journal, Mar. 2007, vol. 22, pp. 659-661, doi: 10.1096/fj.07-9574LSF.

Rich, N. E., et al., "Racial and Ethnic Disparities in Nonalcoholic Fatty Liver Disease Prevalence, Severity, and Outcomes in the United States: A Systematic Review and Meta-analysis," Clinical Gastroenterology and Hepatology 2018, 16, 198-210, 210.e1-210. e2.

Rinella, M. E., et al., "AASLD Practice Guidance on the clinical assessment and management of nonalcoholic fatty liver disease," Hepatology 2023, 77, 1797-1835.

Romero, F., et al., "The Race to Bash NASH: Emerging Targets and Drug Development in a Complex Liver Disease," Journal of Medicinal Chemistry, 2020, 63:5031-5073, doi: 10.1021/acs.jmedchem. 9b01701.

Schwimmer, et al., "Prevalence of Fatty Liver in Children and Adolescents," Pediatrics, 2006, 118:1388-1393.

Shepherd, E.L. et al., "Inhibition Of Vascular Adhesion Protein-1 Modifies Hepatic Steatosis In Vitro And In Vivo", World Journal of Hepatology, 12(11):931-948 (Nov. 27, 2020).

Simone, J. V. (1996) "Introduction" in Cecil Textbook of Medicine. 20th Ed., vol. I . J. Claude Bennet and F. Plum (Eds.) W.B. Sauders Co.; pp. 1004-1010.

Sinha, R. A. et al., "Direct Effects of Thyroid Hormones on Hepatic Lipid Metabolism," Nat. Rev. Endocrinology, May 2018, 14(5):259-269 (26 total pages).

Sinha, R. A., et al., "Nonalcoholic Fatty Liver Disease and Hypercholesterolemia: Roles of Thyroid Hormones, Metabolites, and Agonists," Thyroid 2019, vol. 29, No. 9, pp. 1173-1191, DOI: 10.1089/thy.2018.0664.

Stine, J. G., et al., "Change in MRI-PDFF and Histologic Response in Patients with Nonalcoholic Steatohepatitis: A Systematic Review and Meta-Analysis," Clinical Gastroenterology and Hepatology 2021, vol. 19, No. 11, 2274-2283, 2283.e1-2283.e5.

Sumida, Y., et al., "Current and new pharmacotherapy options for non-alcoholic steatohepatitis", Expert Opinion on Pharmacotherapy, vol. 21, No. 8, Apr. 1, 2020, pp. 953-967, DOI: 10.1080/14656566. 2020.1744564.

Taub, R., et al., 'Lipid lowering in healthy volunteers treated with multiple doses of MGL-3196, a liver-targeted thyroid hormone receptor-β agonist,' Atherosclerosis, 2013, 230:373-80.

U.S. Appl. No. 17/305,302, filed Jul. 2, 2021, by Shanghai Yu et al. (A copy of the U.S. Patent application is not submitted herewith pursuant lo the waiver of 37 C.F.R. § 1.98(a)(2){iii) issued by the Office on Sep. 21, 2004.).

U.S. Appl. No. 18/818,705, filed Aug. 29, 2024, by Kirschberg et al.

U.S. Appl. No. 19/052,553, filed Feb. 13, 2025, by Yu, Shanghai et al.

U.S. Appl. No. 19/052,557, filed Feb. 13, 2025, by Yu, Shanghai et al.

(56) References Cited

OTHER PUBLICATIONS

Vuppalanchi, R et al., "Therapeutic pipeline in nonalcoholic steatohepatitis," Nature Reviews Gastroenterology, Feb. 2021, vol. 18, No. 6, pp. 373-392, doi: 10.1038/S41575-020-00408-Y.
Walenbergh S. A., et al., "Cholesterol is a significant risk factor for nonalcoholic steatohepatitis," Expert Review of Gastroenterology & Hepatology, 2015, 9(11):1343-1346.

THYROID HORMONE RECEPTOR BETA AGONIST COMPOUNDS

CROSS REFERENCE TO RELATED APPLICATIONS

This application is a national stage application under 35 U.S.C. § 371 of International Application No. PCT/US2020/050497, filed internationally on Sep. 11, 2020, which claims priority to U.S. Provisional Application No. 62/899,581, filed on Sep. 12, 2019, the contents of which are incorporated herein by reference in their entirety.

FIELD OF THE INVENTION

This invention relates to compounds, preferably thyroid hormone receptor beta (THR beta) agonist compounds, compositions thereof, and methods of their preparation, and methods of agonizing THR beta and methods for treating disorders mediated by THR beta.

STATE OF THE ART

The beneficial effects arising from treating hyperthyroid or hypothyroid patients with T3/T4 endogenous ligands or early analogs of these endogenous ligands have been described in the literature (Richardson Hill Jr., S. et al. *J. Clin. Invest.* 1960, 39, 523-533). These early studies, as well as similar follow-up studies, established the heart as a major organ for the manifestation of side effects of both hyperthyroidism and hypothyroidism (Klein, I. et al. *Circulation*, 2007, 1725-1735). In particular, tachycardia, hypertrophism, atrial dysrhythmias, and atrial fibrillation are serious concerns. In addition, increased bone turn-over leading to decreased bone mineral density has also been noted. Negative effects at both sites, heart and bone, have been linked to the agonism of the THR alpha isoform, whereas the beneficial effects of THR agonism in the liver are largely linked to the THR beta isoform (Sinha, R. A. et al. *Nat. Rev. Endocrinology* 2018, 14, 259-269).

Diseases or disorders associated with THR beta include non-alcoholic steatohepatitis (NASH), non-alcoholic fatty liver disease (NAFLD), metabolic syndrome, dyslipidemia, hypertriglyceridemia, and hypercholesterolemia. There is a need for thyroid hormone analogs, such as those that are THR beta agonists, and preferably those that avoid the undesirable effects of hyperthyroidism and hypothyroidism, and maintain the beneficial effects of thyroid hormones, e.g., for the treatment for patients with non-alcoholic steatohepatitis (NASH). In particular, there is a need to develop new thyroid hormone analogs that are selective agonists for THR beta, and preferably those that avoid the undesirable effects associated with agonism of THR alpha, and maintain the beneficial effects of thyroid hormones, e.g., for the treatment for patients with non-alcoholic steatohepatitis (NASH), non-alcoholic fatty liver disease (NAFLD), metabolic syndrome, dyslipidemia, hypertriglyceridemia, or hypercholesterolemia.

SUMMARY

In one aspect, provided herein is a compound of formula (I):

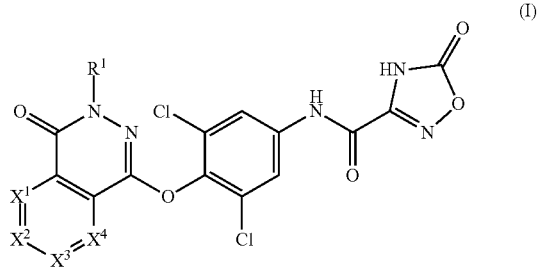

or a tautomer thereof, or a pharmaceutically acceptable salt of any of the foregoing, wherein:

$R^1$ is H or $-CH_3$;

$X^1$, $X^2$, $X^3$, and $X^4$ are each independently $CR^2$ or N, wherein at least two of $X^1$, $X^2$, $X^3$, and $X^4$ are $CR^2$;

each $R^2$ is independently H, halo, $C_1$-$C_6$ alkyl, $C_1$-$C_6$ alkyl-CN, $C_1$-$C_6$ alkyl-OH, $C_1$-$C_6$ haloalkyl, $-CN$, hydroxyl, $-NH_2$, $-NH(C_1$-$C_6$ alkyl), $-N(C_1$-$C_6$ alkyl)$_2$, $-O(C_1$-$C_6$ alkyl), $C_3$-$C_6$ cycloalkyl, 5- to 6-membered heteroaryl, 5- to 7-membered heterocyclyl, or $C_6$ aryl, wherein each $C_1$-$C_6$ alkyl, $-O(C_1$-$C_6$ alkyl), $C_3$-$C_6$ cycloalkyl, 5- to 6-membered heteroaryl, 5- to 7-membered heterocyclyl, or $C_6$ aryl is optionally substituted by 1-5 $R^3$ groups;

or two $R^2$ groups are taken together with the carbon atoms to which they are attached to form a 5- to 6-membered heteroaryl, 5- to 7-membered heterocyclyl, $C_5$-$C_7$ cycloalkyl, or $C_6$ aryl, each of which is optionally substituted by 1-5 $R^3$ groups; and each $R^3$ is independently $C_1$-$C_6$ alkyl, $-O(C_1$-$C_6$ alkyl), halo, $-CN$, hydroxyl, $-NH_2$, $-NH(C_1$-$C_6$ alkyl), $-N(C_1$-$C_6$ alkyl)$_2$, or $CO_2H$.

In some embodiments, $R^1$ is H.

In some embodiments, $R^1$ is $-CH_3$.

In some embodiments, $X^1$, $X^2$, $X^3$, and $X^4$ are each independently $CR^2$. In some embodiments, one of $X^1$, $X^2$, $X^3$, and $X^4$ is N. In some embodiments, two of $X^1$, $X^2$, $X^3$, and $X^4$ are N.

In some embodiments, each $R^2$ is independently H, halo, $C_1$-$C_3$ alkyl, $C_1$-$C_3$ alkyl-CN, $C_1$-$C_3$ alkyl-OH, $C_1$-$C_3$ haloalkyl, $-CN$, hydroxyl, $-NH_2$, $-NH(C_1$-$C_3$ alkyl), $-N(C_1$-$C_3$ alkyl)$_2$, $-O(C_1$-$C_3$ alkyl), $C_3$-$C_6$ cycloalkyl, 5- to 6-membered heteroaryl, 5- to 6-membered heterocyclyl, or $C_6$ aryl, wherein each $C_1$-$C_3$ alkyl, $-O(C_1$-$C_3$ alkyl), $C_3$-$C_6$ cycloalkyl, 5- to 6-membered heteroaryl, 5- to 6-membered heterocyclyl, or $C_6$ aryl is optionally substituted by 1-5 $R^3$ groups. In some embodiments, each $R^2$ is independently H, halo, or $C_1$-$C_3$ alkyl optionally substituted by 1-2 $R^3$ groups. In some embodiments, each $R^2$ is independently H, F, Cl, or $-CH_3$. In some embodiments, each $R^2$ is H. In some embodiments, one or two of $R^2$ are independently selected from the group consisting of halo, $C_1$-$C_3$ alkyl, $C_1$-$C_3$ alkyl-CN, $C_1$-$C_3$ alkyl-OH, $C_1$-$C_6$ haloalkyl, $-CN$, hydroxyl, $-NH_2$, $-NH(C_1$-$C_3$ alkyl), $-N(C_1$-$C_3$ alkyl)$_2$, $-O(C_1$-$C_3$ alkyl), $C_3$-$C_6$ cycloalkyl, 5- to 6-membered heteroaryl, 5- to 6-membered heterocyclyl, and $C_6$ aryl, wherein each $C_1$-$C_3$ alkyl, $-O(C_1$-$C_3$ alkyl), $C_3$-$C_6$ cycloalkyl, 5- to 6-membered heteroaryl, 5- to 6-membered heterocyclyl, or $C_6$ aryl is optionally substituted by 1-5 R³ groups. In some embodiments, two R² groups are taken together with the carbon atoms to which they are attached to form a 5- to 6-membered heteroaryl, 5- to 6-membered heterocyclyl, $C_5$-$C_6$ cycloalkyl, or $C_6$ aryl, each of which is optionally substituted by 1-5 R³ groups.

In some embodiments, each R³, if present, is independently $C_1$-$C_3$ alkyl, —O($C_1$-$C_3$ alkyl), halo, —CN, hydroxyl, —$NH_2$, —NH($C_1$-$C_3$ alkyl), —N($C_1$-$C_3$ alkyl)$_2$, or $CO_2H$. In some embodiments, each R³ is independently $CH_3$, —$OCH_3$, F, Cl, —CN, hydroxyl, —$NH_2$, —NH($CH_3$), —N($CH_3$)$_2$, or $CO_2H$.

In some embodiments, the compound of formula (I) is

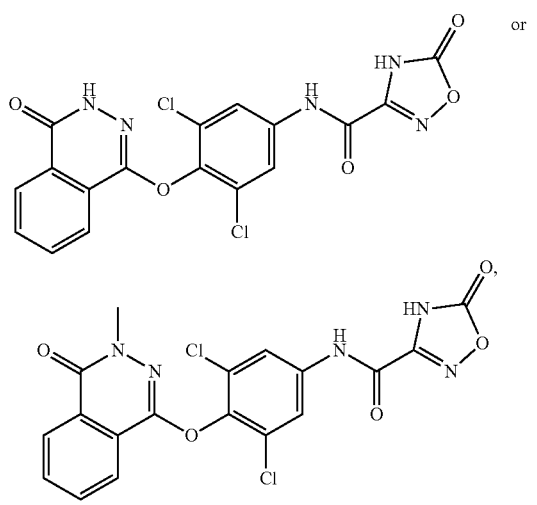

or a tautomer thereof, or a pharmaceutically acceptable salt of any of the foregoing.

In one aspect, provided herein is a pharmaceutical composition comprising a compound as disclosed herein, or a tautomer thereof, or a pharmaceutically acceptable salt of any of the foregoing, and at least one pharmaceutically acceptable excipient.

In one aspect, provided herein is a method of agonizing thyroid hormone receptor beta (THR beta) comprising contacting either an effective amount of a compound as disclosed herein, or a tautomer thereof, or a pharmaceutically acceptable salt of any of the foregoing, or an effective amount of a pharmaceutical composition as disclosed herein, with the THR beta.

In one aspect, provided herein is a method of treating a disorder which is mediated by THR beta in a patient, comprising administering to the patient a therapeutically effective amount of a compound as disclosed herein, or a tautomer thereof, or a pharmaceutically acceptable salt of any of the foregoing, or a therapeutically effective amount of a composition as disclosed herein. In some embodiments, the disorder is non-alcoholic steatohepatitis (NASH).

DETAILED DESCRIPTION

Definitions

As used herein, the following definitions shall apply unless otherwise indicated. Further, if any term or symbol used herein is not defined as set forth below, it shall have its ordinary meaning in the art.

"Comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of, e.g., other ingredients and substantial method steps recited. Embodiments defined by each of these transition terms are within the scope of this invention.

"Effective amount" or dose of a compound or a composition refers to that amount of the compound or the composition that results in an intended result as desired based on the disclosure herein. Effective amounts can be determined by standard pharmaceutical procedures in cell cultures or experimental animals, e.g., and without limitation, by determining the $LD_{50}$ (the dose lethal to 50% of the population) and the $ED_{50}$ (the dose therapeutically effective in 50% of the population).

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Patient" refers to mammals and includes humans and non-human mammals. Examples of patients include, but are not limited to mice, rats, hamsters, guinea pigs, pigs, rabbits, cats, dogs, goats, sheep, cows, and humans. In some embodiments, patient refers to a human.

"Pharmaceutically acceptable" refers to safe and non-toxic, such as for in vivo use or for human administration.

"Pharmaceutically acceptable salt" refers to a salt that is pharmaceutically acceptable. A compound described herein may be administered as a pharmaceutically acceptable salt.

"Salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

"Therapeutically effective amount" or dose of a compound or a composition refers to that amount of the compound or the composition that results in reduction or inhibition of symptoms or a prolongation of survival in a patient. The results may require multiple doses of the compound or the composition.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease. As used herein, "treatment" or "treating" is an approach for obtaining beneficial or desired results including clinical results. For purposes of this invention, beneficial or desired results include, but are not limited to, one or more of the following: decreasing one or more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delaying or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of the invention contemplate any one or more of these aspects of treatment.

An "isotopomer" of a compound is a compound in which one or more atoms of the compound have been replaced with isotopes of those same atoms. For example, where H has been replaced by D or T, or $^{12}C$ has been replaced by $^{11}C$, or $^{14}N$ has been replaced by $^{15}N$. For example, and without limitation, replacement of H with D can in some instances lead to reduced rates of metabolism and therefore longer half-lives. Replacement of H with T can provide radioligands potentially useful in binding studies. Replacement of $^{12}C$ with the short-lived isotope $^{11}C$ can provide ligands useful in Positron Emission Tomography (PET) scanning. Replacement of $^{14}N$ with $^{15}N$ provides compounds that can be detected/monitored by $^{15}N$ NMR spectroscopy. For example, an isotopomer of a compound containing —$CH_2CH_3$ is that compound but containing —$CD_2CD_3$ instead of the —$CH_2CH_3$.

Unless a specific isotope of an element is indicated in a formula, the disclosure includes all isotopologues of the compounds disclosed herein, such as, for example, deuterated derivatives of the compounds (where H can be $^2H$, i.e., D). Isotopologues can have isotopic replacements at any or at all locations in a structure, or can have atoms present in natural abundance at any or all locations in a structure.

"Stereoisomer" or "stereoisomers" refer to compounds that differ in the stereogenicity of the constituent atoms such as, without limitation, in the chirality of one or more stereocenters or related to the cis or trans configuration of a carbon-carbon or carbon-nitrogen double bond. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Alkyl" refers to monovalent saturated aliphatic hydrocarbyl groups having from 1 to 12 carbon atoms, such as from 1 to 10 carbon atoms, and from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2$CH—), n-butyl ($CH_3CH_2CH_2CH_2$—), isobutyl (($CH_3)_2$CHCH$_2$—), sec-butyl (($CH_3)(CH_3CH_2)$CH—), t-butyl (($CH_3)_3C$—), n-pentyl ($CH_3CH_2CH_2CH_2CH_2$—), and neopentyl (($CH_3)_3CCH_2$—). $C_x$ alkyl refers to an alkyl group having x number of carbon atoms.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Amino" refers to the group —$NH_2$.

"Aryl" or "Ar" refers to an aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Exemplary aryl groups include phenyl and naphthyl. It is understood that aryl groups are typically monovalent but can be bivalent when part of a fused condensed ring structure.

"Carbonyl" refers to the divalent group —C(O)— which is equivalent to —C(=O)—.

"Carboxy" or "carboxyl" refers to —COOH or salts thereof.

"Cyano" refers to the group —C≡N.

"Cycloalkyl" refers to saturated or unsaturated but non-aromatic cyclic alkyl groups of from 3 to 10 carbon atoms, from 3 to 8 carbon atoms, and from 3 to 6 carbon atoms, having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. It is understood that cycloalkyl groups are typically monovalent but can be bivalent when part of a fused condensed ring structure.

"Halo" or "halogen" refers to fluoro, chloro, bromo and iodo. In some embodiments, the halogen is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Exemplary heteroaryls include 5 or 6 membered heteroaryls such as pyridinyl, pyrrolyl, thiophenyl, and furanyl. Other exemplary heteroaryls include 9 or 10 membered heteroaryls, such as indolyl, quinolinyl, quinolonyl, isoquinolinyl, and isoquinolonyl. It is understood that heteroaryl groups are typically monovalent but can be bivalent when part of a fused condensed ring structure.

"Heterocycle" or "heterocyclic" or "heterocycloalkyl" or "heterocyclyl" refers to a saturated or partially saturated, but not aromatic, group having from 1 to 10 ring carbon atoms, from 1 to 8 carbon atoms, or from 1 to 6 carbon atoms, and from 1 to 4 ring heteroatoms, from 1 to 3 heteroatoms, or from 1 to 2 heteroatoms selected from the group consisting of nitrogen, sulfur, or oxygen. $C_x$ heterocycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties. It is understood that heterocyclic groups are typically monovalent but can be bivalent when part of a fused condensed ring structure.

Examples of heterocyclyl and heteroaryl include, but are not limited to, azetidinyl, pyrrolyl, imidazolyl, pyrazolyl, pyridyl, pyrazyl, pyrimidyl, pyridazyl, indolizyl, isoindolyl, indolyl, dihydroindolyl, indazolyl, purinyl, quinolizinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, isoxazolyl, phenoxazinyl, phenothiazinyl, imidazolidinyl, imidazolinyl, piperidinyl, piperazinyl, indolinyl, phthalimidyl, 1,2,3,4-tetrahydroisoquinolinyl, 4,5,6,7-tetrahydrobenzo[b]thiophenyl, thiazolyl, thiazolidinyl, thiophenyl, benzo[b]thiophenyl, morpholinyl, thiomorpholinyl (also referred to as thiamorpholinyl), 1,1-dioxothiomorpholinyl, piperidinyl, pyrrolidinyl, and tetrahydrofuranyl.

"Oxo" refers to the atom (=O) or (O).

The terms "optional" or "optionally" as used throughout the specification means that the subsequently described event or circumstance may but need not occur, and that the description includes instances where the event or circumstance occurs and instances in which it does not. For example, "$C_1$-$C_3$ alkyl optionally substituted by 1-2 $R^3$ groups" means that the $C_1$-$C_3$ alkyl may but need not be substituted by 1-2 $R^3$ groups, and the description includes situations where the $C_1$-$C_3$ alkyl is not substituted by a $R^3$ group, situations where the $C_1$-$C_3$ alkyl is substituted by one $R^3$ group, and situations where the $C_1$-$C_3$ alkyl is substituted by two $R^3$ groups. When multiple substituents are present, each substituent is independently chosen unless indicated otherwise. For example, each ($C_1$-$C_3$ alkyl) substituent on the group —N($C_1$-$C_3$ alkyl)($C_1$-$C_3$ alkyl) can be selected independently from the other, so as to generate groups such as —N(CH$_3$)(CH$_2$CH$_3$), etc.

In addition to the disclosure herein, the term "substituted", when used to modify a specified group or radical, can also mean that one or more hydrogen atoms of the specified group or radical are each, independently of one another, replaced with the same or different substituent groups as defined herein. In some embodiments, a group that is substituted has 1, 2, 3, or 4 substituents, 1, 2, or 3 substituents, 1 or 2 substituents, or 1 substituent.

Substituents can be attached to any chemically possible location on the specified group or radical, unless indicated otherwise. Thus, —$C_1$-$C_3$ alkyl-OH includes, for example, —CH$_2$CH$_2$OH and —CH(OH)—CH$_3$.

It is understood that the above definitions are not intended to include impermissible substitution patterns (e.g., methyl substituted with 4 fluoro groups). Such impermissible substitution patterns are well known to the skilled artisan.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Compounds

In one aspect, provided herein is a compound of formula (I):

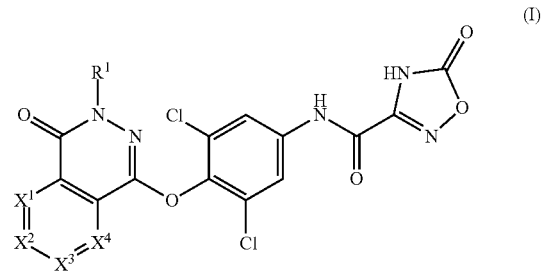

or a tautomer thereof, or a pharmaceutically acceptable salt of any of the foregoing, wherein:

$R^1$ is H or —CH$_3$;

$X^1$, $X^2$, $X^3$ and $X^4$ are each independently CR$^2$ or N, wherein at least two of $X^1$, $X^2$, $X^3$, and $X^4$ are CR$^2$;

each $R^2$ is independently H, halo, $C_1$-$C_6$ alkyl, $C_1$-$C_6$ alkyl-CN, $C_1$-$C_6$ alkyl-OH, $C_1$-$C_6$ haloalkyl, —CN, hydroxyl, —NH$_2$, —NH($C_1$-$C_6$ alkyl), —N($C_1$-$C_6$ alkyl)$_2$, —O($C_1$-$C_6$ alkyl), $C_3$-$C_6$ cycloalkyl, 5- to 6-membered heteroaryl, 5- to 7-membered heterocyclyl, or $C_6$ aryl, wherein each $C_1$-$C_6$ alkyl, —O($C_1$-$C_6$ alkyl), $C_3$-$C_6$ cycloalkyl, 5- to 6-membered heteroaryl, 5- to 7-membered heterocyclyl, or $C_6$ aryl is optionally substituted by 1-5 $R^3$ groups;

or two $R^2$ groups are taken together with the carbon atoms to which they are attached to form a 5- to 6-membered heteroaryl, 5- to 7-membered heterocyclyl, $C_5$-$C_7$ cycloalkyl, or $C_6$ aryl, each of which is optionally substituted by 1-5 $R^3$ groups; and each $R^3$ is independently $C_1$-$C_6$ alkyl, —O($C_1$-$C_6$ alkyl), halo, —CN, hydroxyl, —$NH_2$, —NH($C_1$-$C_6$ alkyl), —N($C_1$-$C_6$ alkyl)$_2$, or $CO_2H$.

In some embodiments, the compound of formula (I) is a pharmaceutically acceptable salt thereof.

In some embodiments, $R^1$ is H or —$CH_3$. In one embodiment, $R^1$ is H. In some embodiments, $R^1$ is —$CH_3$.

In some embodiments, $X^1$, $X^2$, $X^3$, and $X^4$ are each independently $CR^2$ or N, wherein at least two of $X^1$, $X^2$, $X^3$, and $X^4$ are $CR^2$. In some embodiments, $X^1$, $X^2$, $X^3$, and $X^4$ are each independently $CR^2$. In some embodiments, three of $X^1$, $X^2$, $X^3$, and $X^4$ are independently $CR^2$. In some embodiments, one of $X^1$, $X^2$, $X^3$, and $X^4$ is N. In some embodiments, two of $X^1$, $X^2$, $X^3$, and $X^4$ are independently $CR^2$. In some embodiments, two of $X^1$, $X^2$, $X^3$, and $X^4$ are N. In some embodiments, three of $X^1$, $X^2$, $X^3$, and $X^4$ are independently $CR^2$, and one of $X^1$, $X^2$, $X^3$, and $X^4$ is N. In some embodiments, two of $X^1$, $X^2$, $X^3$, and $X^4$ are independently $CR^2$, and two of $X^1$, $X^2$, $X^3$, and $X^4$ are N. In some embodiments, $X^1$, $X^2$, and $X^3$ are independently $CR^2$, and $X^4$ is N. In some embodiments, $X^1$, $X^2$, and $X^4$ are independently $CR^2$, and $X^3$ is N. In some embodiments, $X^1$, $X^3$, and $X^4$ are independently $CR^2$, and $X^2$ is N. In some embodiments, $X^2$, $X^3$, and $X^4$ are independently $CR^2$, and $X^1$ is N. In some embodiments, $X^1$ and $X^2$ are independently $CR^2$, and $X^3$ and $X^4$ are each N. In some embodiments, $X^1$ and $X^3$ are independently $CR^2$, and $X^2$ and $X^4$ are each N. In some embodiments, $X^1$ and $X^4$ are independently $CR^2$, and $X^2$ and $X^3$ are each N. In some embodiments, $X^2$ and $X^3$ are independently $CR^2$, and $X^1$ and $X^4$ are each N. In some embodiments, $X^2$ and $X^4$ are independently $CR^2$, and $X^1$ and $X^3$ are each N. In some embodiments, $X^3$ and $X^4$ are independently $CR^2$, and $X^1$ and $X^2$ are each N. In some embodiments, the

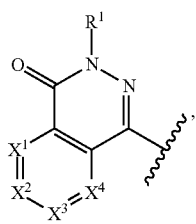

moiety is

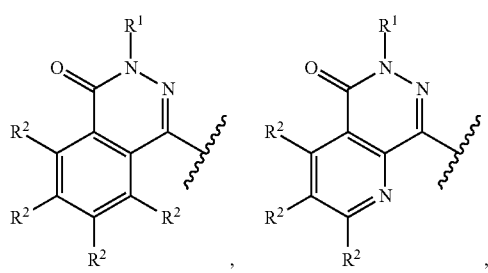

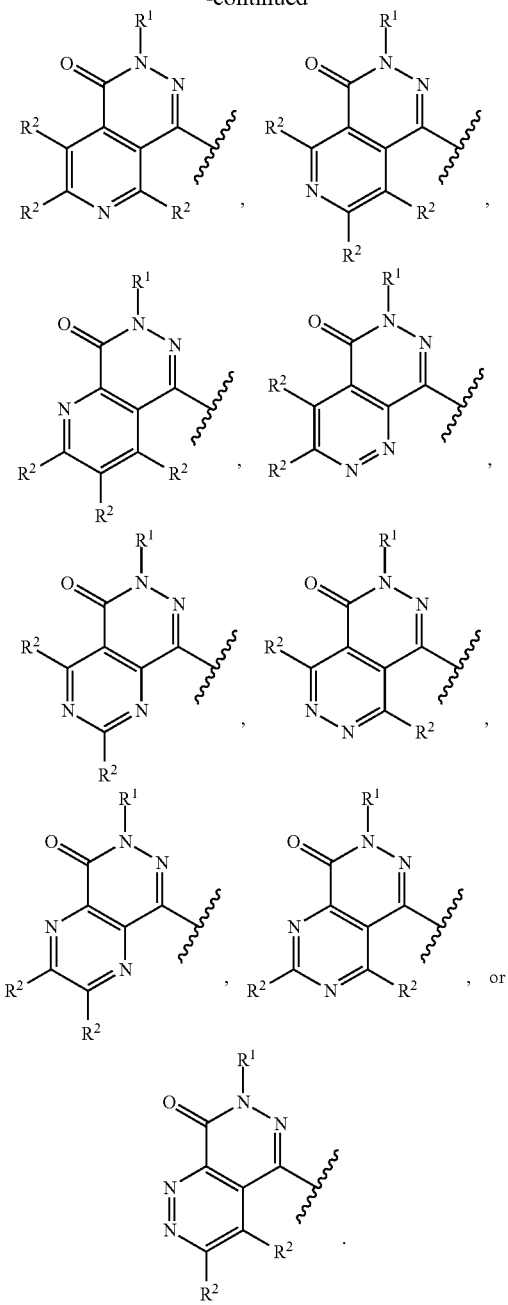

In some embodiments, each $R^2$ is independently H, halo, $C_1$-$C_6$ alkyl, $C_1$-$C_6$ alkyl-CN, $C_1$-$C_6$ alkyl-OH, $C_1$-$C_6$ haloalkyl, —CN, hydroxyl, —$NH_2$, —NH($C_1$-$C_6$ alkyl), —N($C_1$-$C_6$ alkyl)$_2$, —O($C_1$-$C_6$ alkyl), $C_3$-$C_6$ cycloalkyl, 5- to 6-membered heteroaryl, 5- to 7-membered heterocyclyl, or $C_6$ aryl, wherein each $C_1$-$C_6$ alkyl, -O($C_1$-$C_6$ alkyl), $C_3$-$C_6$ cycloalkyl, 5- to 6-membered heteroaryl, 5- to 7-membered heterocyclyl, or $C_6$ aryl is optionally substituted by 1-5 $R^3$ groups; or two $R^2$ groups are taken together with the carbon atoms to which they are attached to form a 5- to 6-membered heteroaryl, 5- to 7-membered heterocyclyl, $C_5$-$C_7$ cycloalkyl, or $C_6$ aryl, each of which is optionally substituted by 1-5 $R^3$ groups.

In some embodiments, each $R^2$ is independently H, halo, $C_1$-$C_3$ alkyl, $C_1$-$C_3$ alkyl-CN, $C_1$-$C_3$ alkyl-OH, $C_1$-$C_3$ haloalkyl, —CN, hydroxyl, —NH$_2$, —NH(C$_1$-C$_3$ alkyl), —N(C$_1$-C$_3$ alkyl)$_2$, —O(C$_1$-C$_3$ alkyl), C$_3$-C$_6$ cycloalkyl, 5- to 6-membered heteroaryl, 5- to 6-membered heterocyclyl, or C$_6$ aryl, wherein each C$_1$-C$_3$ alkyl, —O(C$_1$-C$_3$ alkyl), C$_3$-C$_6$ cycloalkyl, 5- to 6-membered heteroaryl, 5- to 6-membered heterocyclyl, or C$_6$ aryl is optionally substituted by 1-5 R$^3$ groups. In some embodiments, each R$^2$ is independently H, halo, or C$_1$-C$_3$ alkyl optionally substituted by 1-2 R$^3$ groups. In some embodiments, each R$^2$ is independently H, F, Cl, or —CH$_3$. In some embodiments, each R$^2$ is H. In some embodiments, one or two of R$^2$ are independently selected from the group consisting of halo, C$_1$-C$_3$ alkyl, C$_1$-C$_3$ alkyl-CN, C$_1$-C$_3$ alkyl-OH, C$_1$-C$_6$ haloalkyl, —CN, hydroxyl, —NH$_2$, —NH(C$_1$-C$_3$ alkyl), —N(C$_1$-C$_3$ alkyl)$_2$, —O(C$_1$-C$_3$ alkyl), C$_3$-C$_6$ cycloalkyl, 5- to 6-membered heteroaryl, 5- to 6-membered heterocyclyl, and C$_6$ aryl, wherein each C$_1$-C$_3$ alkyl, -O(C$_1$-C$_3$ alkyl), C$_3$-C$_6$ cycloalkyl, 5- to 6-membered heteroaryl, 5- to 6-membered heterocyclyl, or C$_6$ aryl is optionally substituted by 1-5 R$^3$ groups. In some embodiments, two R$^2$ groups are taken together with the carbon atoms to which they are attached to form a 5- to 6-membered heteroaryl, 5- to 6-membered heterocyclyl, C$_5$-C$_6$ cycloalkyl, or C$_6$ aryl, each of which is optionally substituted by 1-5 R$^3$ groups.

In some embodiments, R$^2$ is H. In some variations, at least one R$^2$ is H and at least one R$^2$ is C$_1$-C$_6$ alkyl or halo. In some variations, at least one R$^2$ is H and at least one R$^2$ is C$_1$-C$_6$ alkyl. In some variations, at least one R$^2$ is H and at least one R$^2$ is halo. In some embodiments, each R$^2$ is H.

In some embodiments, R$^2$ is halo. In some embodiments, R$^2$ is F, Cl, or Br. In some embodiments, R$^2$ is F or Cl.

In some embodiments, R$^2$ is C$_1$-C$_6$ alkyl optionally substituted by 1-5 R$^3$ groups. In some embodiments, R$^2$ is C$_1$-C$_6$ alkyl substituted by 1-5 R$^3$ groups. In some embodiments, R$^2$ is C$_1$-C$_6$ alkyl substituted by 1 R$^3$ group. In some embodiments, R$^2$ is C$_1$-C$_6$ alkyl substituted by 2 R$^3$ groups. In some embodiments, R$^2$ is C$_1$-C$_6$ alkyl substituted by 3 R$^3$ groups. In some embodiments, R$^2$ is C$_1$-C$_6$ alkyl substituted by 4 R$^3$ groups. In some embodiments, R$^2$ is C$_1$-C$_6$ alkyl substituted by 5 R$^3$ groups. In some embodiments, R$^2$ is C$_1$-C$_3$ alkyl optionally substituted by 1-2 R$^3$ groups. In some embodiments, R$^2$ is unsubstituted C$_1$-C$_6$ alkyl. In some embodiments, R$^2$ is unsubstituted C$_1$-C$_3$ alkyl, such as methyl, ethyl, n-propyl, or isopropyl. In some embodiments, R$^2$ is —CH$_3$.

In some embodiments, R$^2$ is C$_1$-C$_6$ alkyl-CN. In some embodiments, R$^2$ is C$_1$-C$_3$ alkyl-CN, such as methyl-CN, ethyl-CN, n-propyl-CN, or isopropyl-CN. In some embodiments, R$^2$ is —CH$_2$CN, —CH$_2$CH$_2$CN, —CH(CN)CH$_3$, —CH$_2$CH$_2$CH$_2$CN, —CH$_2$CH(CN)CH$_3$, —CH(CN)CH$_2$CH$_3$, —CH(CH$_3$)CH$_2$CN, or —C(CH$_3$)$_2$CN. In some embodiments, R$^2$ is —CH$_2$CN.

In some embodiments, R$^2$ is C$_1$-C$_6$ alkyl-OH. In some embodiments, R$^2$ is C$_1$-C$_3$ alkyl-OH, such as methyl-OH, ethyl-OH, n-propyl-OH, or isopropyl-OH. In some embodiments, R$^2$ is —CH$_2$OH, —CH$_2$CH$_2$OH, —CH(OH)CH$_3$, —CH$_2$CH$_2$CH$_2$OH, —CH$_2$CH(OH)CH$_3$, —CH(OH)CH$_2$CH$_3$, —CH(CH$_3$)CH$_2$OH, or —C(CH$_3$)$_2$OH. In some embodiments, R$^2$ is —CH$_2$OH.

In some embodiments, R$^2$ is C$_1$-C$_6$ haloalkyl. In some embodiments, R$^2$ is C$_1$-C$_6$ haloalkyl containing 1-7 halogen atoms. In some embodiments, R$^2$ is C$_1$-C$_3$ haloalkyl. In some embodiments, R$^2$ is C$_1$-C$_3$ haloalkyl containing 1-5 halogen atoms. In some embodiments, R$^2$ is C$_1$-C$_3$ haloalkyl containing 1-3 halogen atoms. In some embodiments, R$^2$ is C$_1$-C$_2$ haloalkyl. In some embodiments, R$^2$ is C$_1$-C$_2$ haloalkyl containing 1-3 halogen atoms. In some embodiments R$^2$ is C$_1$ haloalkyl. In some embodiments R$^2$ is C$_1$ haloalkyl containing 1-3 halogen atoms. In some embodiments, the halogen atoms are independently selected from the group consisting of F, Cl, and Br. In some embodiments, the halogen atoms are independently selected from the group consisting of F and Cl. In some embodiments, the halogen atoms are all F. In some embodiments, the halogen atoms are all Cl. In some embodiments, the halogen atoms are a combination of F and Cl. In some embodiments, R$^2$ is —CH$_2$F, —CHF$_2$, —CF$_3$, —CH$_2$Cl, —CHCl$_2$, —CCl$_3$, —CF$_2$Cl, —CFCl$_2$, or —CHFCl. In some embodiments, R$^2$ is —CF$_3$.

In some embodiments, R$^2$ is —CN. In some embodiments, R$^2$ is hydroxyl. In some embodiments, R$^2$ is —NH$_2$.

In some embodiments, R$^2$ is —NH(C$_1$-C$_6$ alkyl). In some embodiments, R$^2$ is —NH(C$_1$-C$_3$ alkyl), such as —NH(methyl), —NH(ethyl), —NH(n-propyl), or —NH(isopropyl). In some embodiments, R$^2$ is —NH(CH$_3$).

In some embodiments, R$^2$ is —N(C$_1$-C$_6$ alkyl)$_2$, where each C$_1$-C$_6$ alkyl is selected independently. In some embodiments, R$^2$ is —N(C$_1$-C$_3$ alkyl)$_2$, such as —N(CH$_3$)$_2$, —N(CH$_2$CH$_3$)$_2$, —N(CH$_2$CH$_2$CH$_3$)$_2$, —N(CH(CH$_3$)$_2$)$_2$, —N(CH$_3$)CH$_2$CH$_3$, —N(CH$_3$)CH$_2$CH$_2$CH$_3$, —N(CH$_3$)CH(CH$_3$)$_2$, —N(CH$_2$CH$_3$)CH$_2$CH$_2$CH$_3$, —N(CH$_2$CH$_3$)CH(CH$_3$)$_2$, or —N(CH$_2$CH$_2$CH$_3$)CH(CH$_3$)$_2$. In some embodiments, R$^2$ is —N(CH$_3$)$_2$.

In some embodiments, R$^2$ is —O(C$_1$-C$_6$ alkyl) optionally substituted by 1-5 R$^3$ groups. In some embodiments, R$^2$ is —O(C$_1$-C$_6$ alkyl) substituted by 1-5 R$^3$ groups. In some embodiments, R$^2$ is —O(C$_1$-C$_6$ alkyl) substituted by 1 R$^3$ group. In some embodiments, R$^2$ is —O(C$_1$-C$_6$ alkyl) substituted by 2 R$^3$ groups. In some embodiments, R$^2$ is —O(C$_1$-C$_6$ alkyl) substituted by 3 R$^3$ groups. In some embodiments, R$^2$ is —O(C$_1$-C$_6$ alkyl) substituted by 4 R$^3$ groups. In some embodiments, R$^2$ is —O(C$_1$-C$_6$ alkyl) substituted by 5 R$^3$ groups. In some embodiments, R$^2$ is —O(C$_1$-C$_3$ alkyl) optionally substituted by 1-5 R$^3$ groups. In some embodiments, R$^2$ is unsubstituted —O(C$_1$-C$_6$ alkyl). In some embodiments, R$^2$ is unsubstituted —O(C$_1$-C$_3$ alkyl), such as —O(methyl), —O(ethyl), —O(n-propyl), or —O(isopropyl). In some embodiments, R$^2$ is —OCH$_3$.

In some embodiments, R$^2$ is C$_3$-C$_6$ cycloalkyl optionally substituted by 1-5 R$^3$ groups. In some embodiments, R$^2$ is C$_3$-C$_6$ cycloalkyl substituted by 1-5 R$^3$ groups. In some embodiments, R$^2$ is C$_3$-C$_6$ cycloalkyl substituted by 1 R$^3$ group. In some embodiments, R$^2$ is C$_3$-C$_6$ cycloalkyl substituted by 2 R$^3$ groups. In some embodiments, R$^2$ is C$_3$-C$_6$ cycloalkyl substituted by 3 R$^3$ groups. In some embodiments, R$^2$ is C$_3$-C$_6$ cycloalkyl substituted by 4 R$^3$ groups. In some embodiments, R$^2$ is C$_3$-C$_6$ cycloalkyl substituted by 5 R$^3$ groups. In some embodiments, R$^2$ is C$_3$-C$_5$ cycloalkyl optionally substituted by 1-5 R$^3$ groups. In some embodiments, R$^2$ is unsubstituted C$_3$-C$_5$ cycloalkyl, such as cyclopropyl, cyclobutyl, or cyclopentyl. In some embodiments, R$^2$ is unsubstituted cyclopropyl.

In some embodiments, R$^2$ is 5- to 6-membered heteroaryl optionally substituted by 1-5 R$^3$ groups. In some embodiments, R$^2$ is 5- to 6-membered heteroaryl containing 1-3 heteroatoms selected from the group consisting of N, O, and S, wherein the heteroaryl is optionally substituted by 1-5 R$^3$ groups. In some embodiments, R$^2$ is 5- to 6-membered heteroaryl containing 1-3 heteroatoms selected from the group consisting of N, O, and S. In some embodiments, R$^2$ is 5- to 6-membered heteroaryl containing 1-2 heteroatoms selected from the group consisting of N, O, and S. In some embodiments, R$^2$ is 5- to 6-membered heteroaryl containing one, two, or three nitrogen atoms. In some embodiments, R$^2$ is 5- to 6-membered heteroaryl containing one nitrogen atom. In some embodiments, R² is 5- to 6-membered heteroaryl containing one, two, or three oxygen atoms. In some embodiments, R² is 5- to 6-membered heteroaryl containing one oxygen atom. In some embodiments, R² is 5- to 6-membered heteroaryl containing one, two, or three sulfur atoms. In some embodiments, R² is 5- to 6-membered heteroaryl containing one sulfur atom. In some embodiments, R² is 5- to 6-membered heteroaryl containing one nitrogen atom and two oxygen atoms. In some embodiments, R² is 5- to 6-membered heteroaryl containing two nitrogen atoms and one oxygen atom. In some embodiments, R² is 5- to 6-membered heteroaryl containing one nitrogen atom and one oxygen atom. In some embodiments, R² is 5- to 6-membered heteroaryl containing one nitrogen atom and two sulfur atoms. In some embodiments, R² is 5- to 6-membered heteroaryl containing two nitrogen atoms and one sulfur atom. In some embodiments, R² is 5- to 6-membered heteroaryl containing one nitrogen atom and one sulfur atom. In some embodiments, R² is 5- to 6-membered heteroaryl containing one oxygen atom and two sulfur atoms. In some embodiments, R² is 5- to 6-membered heteroaryl containing two oxygen atoms and one sulfur atom. In some embodiments, R² is 5- to 6-membered heteroaryl containing one oxygen atom and one sulfur atom. In some embodiments, R² is pyrrolyl, pyrazolyl, imidazolyl, triazolyl, furanyl, thiophenyl, oxazolyl, thiazolyl, pyridinyl, pyridazinyl, pyrimidinyl, or pyrazinyl. In some embodiments, R² is 5- to 6-membered heteroaryl, including any variation detailed herein, optionally substituted by 1-5 R³ groups. In some embodiments, R² is 5- to 6-membered heteroaryl substituted by 1-5 R³ groups. In some embodiments, R² is 5- to 6-membered heteroaryl substituted by 1 R³ group. In some embodiments, R² is 5- to 6-membered heteroaryl substituted by 2 R³ groups. In some embodiments, R² is 5- to 6-membered heteroaryl substituted by 3 R³ groups. In some embodiments, R² is 5- to 6-membered heteroaryl substituted by 4 R³ groups. In some embodiments, R² is 5- to 6-membered heteroaryl substituted by 5 R³ groups. In some embodiments, R² is unsubstituted 5- to 6-membered heteroaryl, including any variation detailed herein.

In some embodiments, R² is 5- to 7-membered heterocyclyl optionally substituted by 1-5 R³ groups. In some embodiments, R² is 5- to 6-membered heterocyclyl optionally substituted by 1-5 R³ groups. In some embodiments, R² is 5- to 6-membered heterocyclyl containing 1-3 heteroatoms selected from the group consisting of N, O, and S, wherein the heterocyclyl is optionally substituted by 1-5 R³ groups. In some embodiments, R² is 5- to 6-membered heterocyclyl containing 1-3 heteroatoms selected from the group consisting of N, O, and S. In some embodiments, R² is 5- to 6-membered heterocyclyl containing 1-2 heteroatoms selected from the group consisting of N, O, and S. In some embodiments, R² is 5- to 6-membered heterocyclyl containing one, two, or three nitrogen atoms. In some embodiments, R² is 5- to 6-membered heterocyclyl containing one nitrogen atom. In some embodiments, R² is 5- to 6-membered heterocyclyl containing one, two, or three oxygen atoms. In some embodiments, R² is 5- to 6-membered heterocyclyl containing one oxygen atom. In some embodiments, R² is 5- to 6-membered heterocyclyl containing one, two, or three sulfur atoms. In some embodiments, R² is 5- to 6-membered heterocyclyl containing one sulfur atom. In some embodiments, R² is 5- to 6-membered heterocyclyl containing one nitrogen atom and two oxygen atoms. In some embodiments, R² is 5- to 6-membered heterocyclyl containing two nitrogen atoms and one oxygen atom. In some embodiments, R² is 5- to 6-membered heterocyclyl containing one nitrogen atom and one oxygen atom. In some embodiments, R² is 5- to 6-membered heterocyclyl containing one nitrogen atom and two sulfur atoms. In some embodiments, R² is 5- to 6-membered heterocyclyl containing two nitrogen atoms and one sulfur atom. In some embodiments, R² is 5- to 6-membered heterocyclyl containing one nitrogen atom and one sulfur atom. In some embodiments, R² is 5- to 6-membered heterocyclyl containing one oxygen atom and two sulfur atoms. In some embodiments, R² is 5- to 6-membered heterocyclyl containing two oxygen atoms and one sulfur atom. In some embodiments, R² is 5- to 6-membered heterocyclyl containing one oxygen atom and one sulfur atom. In some embodiments, R² is

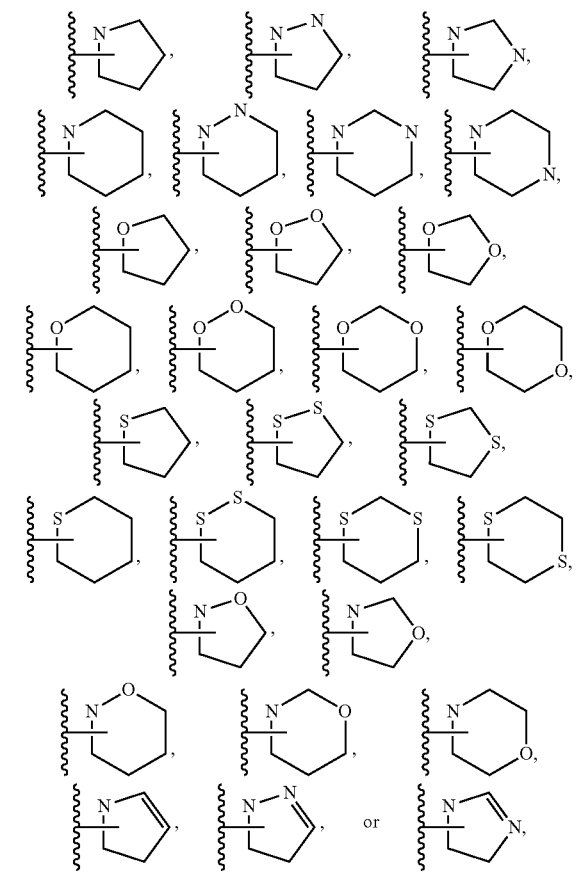

wherein

represents the point of attachment of one carbon atom or one nitrogen atom to the X¹, X², X³, and X⁴ containing ring, and wherein the heteroatoms of the heterocyclyl groups, where applicable, are bound to H when not further substituted. In some embodiments, R² is 5- to 6-membered heterocyclyl, including any variation detailed herein, optionally substituted by 1-5 R³ groups. In some embodiments, R² is 5- to 6-membered heterocycly substituted by 1-5 R³ groups. In some embodiments, $R^2$ is 5- to 6-membered heterocycly substituted by 1 $R^3$ group. In some embodiments, $R^2$ is 5- to 6-membered heterocycly substituted by 2 $R^3$ groups. In some embodiments, $R^2$ is 5- to 6-membered heterocycly substituted by 3 $R^3$ groups. In some embodiments, $R^2$ is 5- to 6-membered heterocycly substituted by 4 $R^3$ groups. In some embodiments, $R^2$ is 5- to 6-membered heterocycly substituted by 5 $R^3$ groups. In some embodiments, $R^2$ is unsubstituted 5- to 6-membered heterocyclyl, including any variation detailed herein.

In some embodiments, $R^2$ is $C_6$ aryl is optionally substituted by 1-5 $R^3$ groups. In some embodiments, $R^2$ is $C_6$ aryl substituted by 1-5 $R^3$ groups. In some embodiments, $R^2$ is $C_6$ aryl substituted by 1 $R^3$ group. In some embodiments, $R^2$ is $C_6$ aryl substituted by 2 $R^3$ groups. In some embodiments, $R^2$ is $C_6$ aryl substituted by 3 $R^3$ groups. In some embodiments, $R^2$ is $C_6$ aryl substituted by 4 $R^3$ groups. In some embodiments, $R^2$ is $C_6$ aryl substituted by 5 $R^3$ groups. In some embodiments, $R^2$ is unsubstituted $C_6$ aryl. In any variation detailed herein, $C_6$ aryl is phenyl.

In some embodiments, two $R^2$ groups are taken together with the carbon atoms to which they are attached to form a 5- to 6-membered heteroaryl, 5- to 7-membered heterocyclyl, $C_5$-$C_7$ cycloalkyl, or $C_6$ aryl, each of which is optionally substituted by 1-5 $R^3$ groups. That is, two $R^2$ groups are taken together with the carbon atoms to which they are attached to form a 5- to 6-membered heteroaryl, 5- to 7-membered heterocyclyl, $C_5$-$C_7$ cycloalkyl, or $C_6$ aryl, each of which is optionally substituted by 1-5 $R^3$ groups, which is fused to the $X^1$, $X^2$, $X^3$, and $X^4$ containing ring to form a tricyclic moiety.

In some embodiments, two $R^2$ groups are taken together with the carbon atoms to which they are attached to form a 5- to 6-membered heteroaryl optionally substituted by 1-5 $R^3$ groups. That is, two $R^2$ groups are taken together with the carbon atoms to which they are attached to form a 5- to 6-membered heteroaryl, optionally substituted by 1-5 $R^3$ groups, which is fused to the $X^1$, $X^2$, $X^3$, and $X^4$ containing ring to form a tricyclic moiety. In some embodiments, the 5- to 6-membered heteroaryl contains 1-3 heteroatoms selected from the group consisting of N, O, and S, wherein the heteroaryl is optionally substituted by 1-5 $R^3$ groups. In some embodiments, the 5- to 6-membered heteroaryl contains 1-3 heteroatoms selected from the group consisting of N, O, and S. In some embodiments, the 5- to 6-membered heteroaryl contains 1-2 heteroatoms selected from the group consisting of N, O, and S. In some embodiments, the 5- to 6-membered heteroaryl contains one, two, or three nitrogen atoms. In some embodiments, the 5- to 6-membered heteroaryl contains one nitrogen atom. In some embodiments, the 5- to 6-membered heteroaryl contains one, two, or three oxygen atoms. In some embodiments, the 5- to 6-membered heteroaryl contains one oxygen atom. In some embodiments, the 5- to 6-membered heteroaryl contains one, two, or three sulfur atoms. In some embodiments, the 5- to 6-membered heteroaryl contains one sulfur atom. In some embodiments, the 5- to 6-membered heteroaryl contains one nitrogen atom and two oxygen atoms. In some embodiments, the 5- to 6-membered heteroaryl contains two nitrogen atoms and one oxygen atom. In some embodiments, the 5- to 6-membered heteroaryl contains one nitrogen atom and one oxygen atom. In some embodiments, the 5- to 6-membered heteroaryl contains one nitrogen atom and two sulfur atoms. In some embodiments, the 5- to 6-membered heteroaryl contains two nitrogen atoms and one sulfur atom. In some embodiments, the 5- to 6-membered heteroaryl contains one nitrogen atom and one sulfur atom. In some embodiments, the 5- to 6-membered heteroaryl contains one oxygen atom and two sulfur atoms. In some embodiments, the 5- to 6-membered heteroaryl contains two oxygen atoms and one sulfur atom. In some embodiments, the 5- to 6-membered heteroaryl contains one oxygen atom and one sulfur atom. In some embodiments, the 5- to 6-membered heteroaryl is

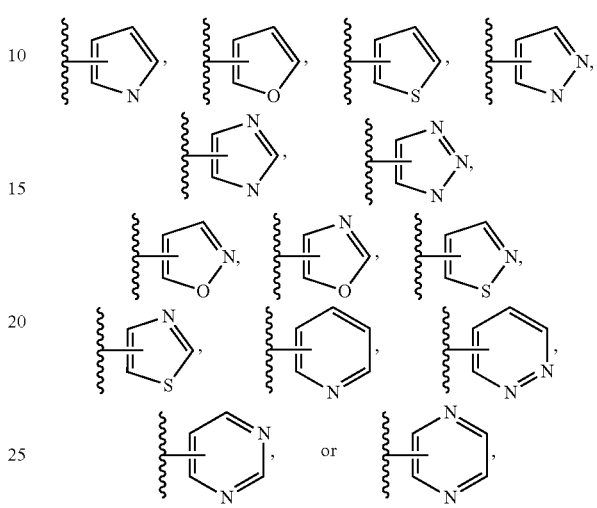

wherein

represents the attachment points where two adjacent carbon atoms are fused to the $X^1$, $X^2$, $X^3$, and $X^4$ containing ring, and wherein the heteroatoms of the heteroaryl groups, where applicable, are bound to H when not further substituted. In some embodiments, the 5- to 6-membered heteroaryl, including any variation detailed herein, is optionally substituted by 1-5 $R^3$ groups. In some embodiments, the 5- to 6-membered heteroaryl is substituted by 1-5 $R^3$ groups. In some embodiments, the 5- to 6-membered heteroaryl is substituted by 1 $R^3$ group. In some embodiments, the 5- to 6-membered heteroaryl is substituted by 2 $R^3$ groups. In some embodiments, the 5- to 6-membered heteroaryl is substituted by 3 $R^3$ groups. In some embodiments, the 5- to 6-membered heteroaryl is substituted by 4 $R^3$ groups. In some embodiments, the 5- to 6-membered heteroaryl is substituted by 5 $R^3$ groups. In some embodiments, 5- to 6-membered heteroaryl, including any variation detailed herein, is unsubstituted.

In some embodiments, two $R^2$ groups are taken together with the carbon atoms to which they are attached to form a 5- to 7-membered heterocyclyl optionally substituted by 1-5 $R^3$ groups. That is, two $R^2$ groups are taken together with the carbon atoms to which they are attached to form a 5- to 7-membered heterocyclyl, optionally substituted by 1-5 $R^3$ groups, which is fused to the $X^1$, $X^2$, $X^3$, and $X^4$ containing ring to form a tricyclic moiety. In some embodiments, the 5- to 7-membered heterocyclyl fused to the $X^1$, $X^2$, $X^3$, and $X^4$ containing ring contains an unsaturated bond between the two carbon atoms which are also part of the $X^1$, $X^2$, $X^3$, and $X^4$ containing ring. In some embodiments, the 5- to 7-membered heterocyclyl fused to the $X^1$, $X^2$, $X^3$, and $X^4$ containing ring contains a saturated bond between the two carbon atoms which are also part of the $X^1$, $X^2$, $X^3$, and $X^4$ containing ring. In some embodiments, the 5- to 7-membered heterocyclyl fused to the $X^1$, $X^2$, $X^3$, and $X^4$ containing ring contains a pi bond between the two carbon atoms which are also part of the $X^1$, $X^2$, $X^3$, and $X^4$ containing ring. In some embodiments, two $R^2$ groups are taken together with the carbon atoms to which they are attached to form a 5- to 6-membered heterocyclyl optionally substituted by 1-5 $R^3$ groups. In some embodiments, the 5- to 7-membered heterocyclyl is optionally substituted by 1-5 $R^3$ groups. In some embodiments, the 5- to 7-membered heterocyclyl contains 1-3 heteroatoms selected from the group consisting of N, O, and S, wherein the heterocyclyl is optionally substituted by 1-5 $R^3$ groups. In some embodiments, the 5- to 7-membered heterocyclyl contains 1-3 heteroatoms selected from the group consisting of N, O, and S. In some embodiments, the 5- to 7-membered heterocyclyl contains 1-2 heteroatoms selected from the group consisting of N, O and S. In some embodiments, the 5- to 7-membered heterocyclyl contains one, two, or three nitrogen atoms. In some embodiments, the 5- to 7-membered heterocyclyl contains one nitrogen atom. In some embodiments, the 5- to 7-membered heterocyclyl contains one, two, or three oxygen atoms. In some embodiments, the 5- to 7-membered heterocyclyl contains one oxygen atom. In some embodiments, the 5- to 7-membered heterocyclyl contains one, two, or three sulfur atoms. In some embodiments, the 5- to 7-membered heterocyclyl contains one sulfur atom. In some embodiments, the 5- to 7-membered heterocyclyl contains one nitrogen atom and two oxygen atoms. In some embodiments, the 5- to 7-membered heterocyclyl contains two nitrogen atoms and one oxygen atom. In some embodiments, the 5- to 7-membered heterocyclyl contains one nitrogen atom and one oxygen atom. In some embodiments, the 5- to 7-membered heterocyclyl contains one nitrogen atom and two sulfur atoms. In some embodiments, the 5- to 7-membered heterocyclyl contains two nitrogen atoms and one sulfur atom. In some embodiments, the 5- to 7-membered heterocyclyl contains one nitrogen atom and one sulfur atom. In some embodiments, the 5- to 7-membered heterocyclyl contains one oxygen atom and two sulfur atoms. In some embodiments, the 5- to 7-membered heterocyclyl contains two oxygen atoms and one sulfur atom. In some embodiments, the 5- to 7-membered heterocyclyl contains one oxygen atom and one sulfur atom. In some embodiments, the 5- to 7-membered heterocyclyl is

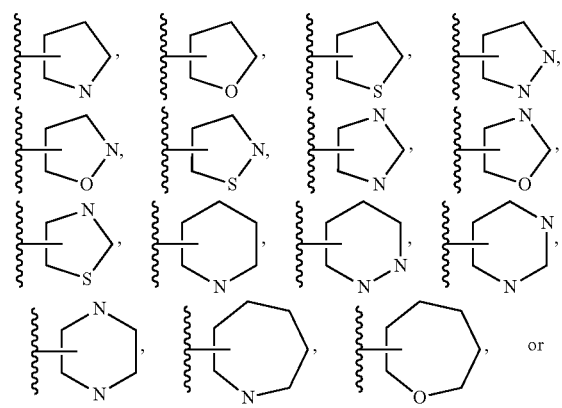

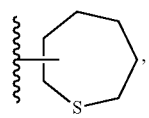

wherein

represents the attachment points where two adjacent carbon atoms are fused to the $X^1$, $X^2$, $X^3$, and $X^4$ containing ring, and wherein the heteroatoms of the heterocyclyl groups, where applicable, are bound to H when not further substituted. In some embodiments, the 5- to 7-membered heterocyclyl, including any variation detailed herein, is optionally substituted by 1-5 $R^3$ groups. In some embodiments, the 5- to 7-membered heterocyclyl is substituted by 1-5 $R^3$ groups. In some embodiments, the 5- to 7-membered heterocyclyl is substituted by 1 $R^3$ group. In some embodiments, the 5- to 7-membered heterocyclyl is substituted by 2 $R^3$ groups. In some embodiments, the 5- to 7-membered heterocyclyl is substituted by 3 $R^3$ groups. In some embodiments, the 5- to 7-membered heterocyclyl is substituted by 4 $R^3$ groups. In some embodiments, the 5- to 7-membered heterocyclyl is substituted by 5 $R^3$ groups. In some embodiments, the 5- to 7-membered heterocyclyl, including any variation detailed herein, is unsubstituted.

In some embodiments, two $R^2$ groups are taken together with the carbon atoms to which they are attached to form a $C_5$-$C_7$ cycloalkyl optionally substituted by 1-5 $R^3$ groups. That is, two $R^2$ groups are taken together with the carbon atoms to which they are attached to form a $C_5$-$C_7$ cycloalkyl, optionally substituted by 1-5 $R^3$ groups, which is fused to the $X^1$, $X^2$, $X^3$, and $X^4$ containing ring to form a tricyclic moiety. In some embodiments, the $C_5$-$C_7$ cycloalkyl fused to the $X^1$, $X^2$, $X^3$, and $X^4$ containing ring contains an unsaturated bond between the two carbon atoms which are also part of the $X^1$, $X^2$, $X^3$, and $X^4$ containing ring. In some embodiments, the $C_5$-$C_7$ cycloalkyl fused to the $X^1$, $X^2$, $X^3$, and $X^4$ containing ring contains a saturated bond between the two carbon atoms which are also part of the $X^1$, $X^2$, $X^3$, and $X^4$ containing ring. In some embodiments, the $C_5$-$C_7$ cycloalkyl fused to the $X^1$, $X^2$, $X^3$, and $X^4$ containing ring contains a pi bond between the two carbon atoms which are also part of the $X^1$, $X^2$, $X^3$, and $X^4$ containing ring. In some embodiments, two $R^2$ groups are taken together with the carbon atoms to which they are attached to form a $C_5$-$C_6$ cycloalkyl optionally substituted by 1-5 $R^3$ groups. In some embodiments, the $C_5$-$C_7$ cycloalkyl is

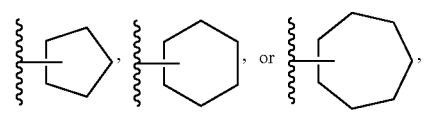

wherein

represents the attachment points where two adjacent carbon atoms are fused to the $X^1$, $X^2$, $X^3$, and $X^4$ containing ring. In some embodiments, the $C_5$-$C_7$ cycloalkyl, including any variation detailed herein, is optionally substituted by 1-5 $R^3$ groups. In some embodiments, the $C_5$-$C_7$ cycloalkyl is substituted by 1-5 $R^3$ groups. In some embodiments, the $C_5$-$C_7$ cycloalkyl is substituted by 1 $R^3$ group. In some embodiments, the $C_5$-$C_7$ cycloalkyl is substituted by 2 $R^3$ groups. In some embodiments, the $C_5$-$C_7$ cycloalkyl is substituted by 3 $R^3$ groups. In some embodiments, the $C_5$-$C_7$ cycloalkyl is substituted by 4 $R^3$ groups. In some embodiments, the $C_5$-$C_7$ cycloalkyl is substituted by 5 $R^3$ groups. In some embodiments, the $C_5$-$C_7$ cycloalkyl, including any variation detailed herein, is unsubstituted.

In some embodiments, two $R^2$ groups are taken together with the carbon atoms to which they are attached to form a $C_6$ aryl optionally substituted by 1-5 $R^3$ groups. That is, two $R^2$ groups are taken together with the carbon atoms to which they are attached to form a $C_6$ aryl, optionally substituted by 1-5 $R^3$ groups, which is fused to the $X^1$, $X^2$, $X^3$, and $X^4$ containing ring to form a tricyclic moiety. In some embodiments, the $C_6$ aryl is

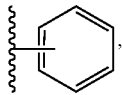

wherein

represents the attachment points where two adjacent carbon atoms are fused to the $X^1$, $X^2$, $X^3$, and $X^4$ containing ring. In some embodiments, two $R^2$ groups are taken together with the carbon atoms to which they are attached to form a $C_6$ aryl substituted by 1-5 $R^3$ groups. In some embodiments, two $R^2$ groups are taken together with the carbon atoms to which they are attached to form a $C_6$ aryl substituted by 1 $R^3$ group. In some embodiments, two $R^2$ groups are taken together with the carbon atoms to which they are attached to form a $C_6$ aryl substituted by 2 $R^3$ groups. In some embodiments, two $R^2$ groups are taken together with the carbon atoms to which they are attached to form a $C_6$ aryl substituted by 3 $R^3$ groups. In some embodiments, two $R^2$ groups are taken together with the carbon atoms to which they are attached to form a $C_6$ aryl substituted by 4 $R^3$ groups. In some embodiments, two $R^2$ groups are taken together with the carbon atoms to which they are attached to form a $C_6$ aryl substituted by 5 $R^3$ groups. In some embodiments, two $R^2$ groups are taken together with the carbon atoms to which they are attached to form a unsubstituted $C_6$ aryl.

In some embodiments, two $R^2$ groups are taken together with the carbon atoms to which they are attached to form a 5- to 6-membered heteroaryl, 5- to 7-membered heterocyclyl, $C_5$-$C_7$ cycloalkyl, or $C_6$ aryl, each of which is optionally substituted by 1-5 $R^3$ groups. In some embodiments, the

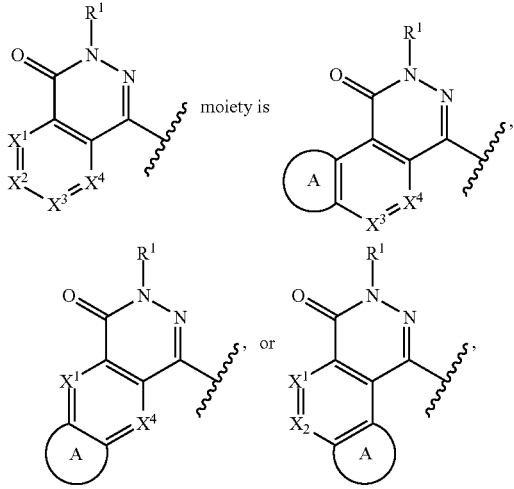

moiety is wherein

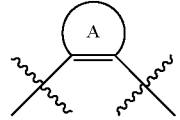

(i.e., the Ring A moiety) is a 5- to 6-membered heteroaryl, 5- to 7-membered heterocyclyl, $C_5$-$C_7$ cycloalkyl, or $C_6$ aryl, each of which is optionally substituted by 1-5 $R^3$ groups, and $X^1$, $X^2$, $X^3$, and $X^4$, as applicable, are as described for the compound of formula (I). In some embodiments, $X^1$, $X^2$, $X^3$, and $X^4$, as applicable, are each independently $CR^2$. In some embodiments, $X^3$ and $X^4$ are each CH. In some embodiments, $X^1$ and $X^4$ are each CH. In some embodiments, $X^1$ and $X^2$ are each CH. In some embodiments, $X^1$, $X^2$, $X^3$, and $X^4$, as applicable, are each N. In some embodiments, $X^3$ and $X^4$ are each N. In some embodiments, $X^1$ and $X^4$ are each N. In some embodiments, $X^1$ and $X^2$ are each N. In some embodiments, one of $X^1$, $X^2$, $X^3$, and $X^4$, as applicable, is $CR^2$ and the other of $X^1$, $X^2$, $X^3$, and $X^4$, as applicable, is N. In some embodiments, the Ring A moiety is a 5-membered heteroaryl, such as

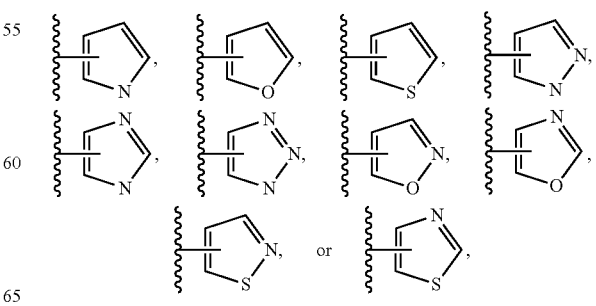

optionally substituted by 1-5 $R^3$ groups, wherein

represents the attachment points where two adjacent carbon atoms are fused to the $X^1$, $X^2$, $X^3$, and $X^4$ containing ring, and wherein the heteroatoms of the heteroaryl groups, where applicable, are bound to H when not further substituted. In some embodiments, the Ring A moiety is a 6-membered heteroaryl, such as

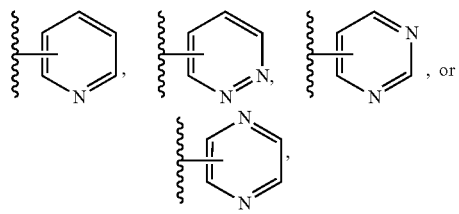

optionally substituted by 1-5 $R^3$ groups, wherein

represents the attachment points where two adjacent carbon atoms are fused to the $X^1$, $X^2$, $X^3$, and $X^4$ containing ring. In some embodiments, the Ring A moiety is a 5-membered heterocyclyl, such as

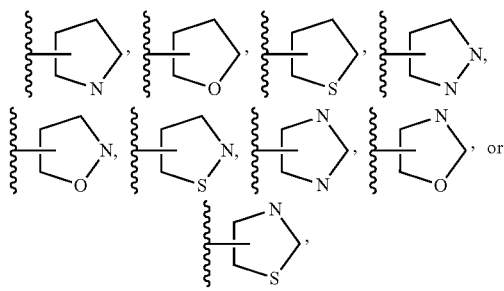

optionally substituted by 1-5 $R^3$ groups, wherein

represents the attachment points where two adjacent carbon atoms are fused to the $X^1$, $X^2$, $X^3$, and $X^4$ containing ring, and wherein the heteroatoms of the heterocyclyl groups, where applicable, are bound to H when not further substituted. In some embodiments, the Ring A moiety is a 6-membered heterocyclyl, such as

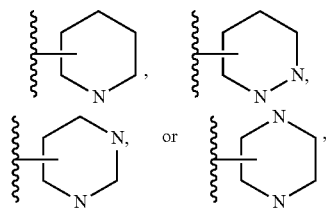

optionally substituted by 1-5 $R^3$ groups, wherein

represents the attachment points where two adjacent carbon atoms are fused to the $X^1$, $X^2$, $X^3$, and $X^4$ containing ring, and wherein the heteroatoms of the heterocyclyl groups, where applicable, are bound to H when not further substituted. In some embodiments, the Ring A moiety is a 7-membered heterocyclyl, such as

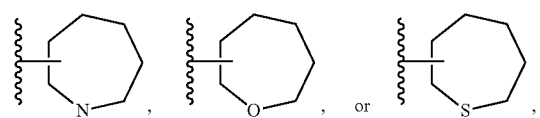

optionally substituted by 1-5 $R^3$ groups, wherein

represents the attachment points where two adjacent carbon atoms are fused to the $X^1$, $X^2$, $X^3$, and $X^4$ containing ring, and wherein the heteroatom of the heterocyclyl group, where applicable, is bound to H when not further substituted. In some embodiments, the Ring A moiety is a $C_5$ cycloalkyl, such as

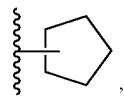

optionally substituted by 1-5 $R^3$ groups, wherein

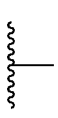

represents the attachment points where two adjacent carbon atoms are fused to the $X^1$, $X^2$, $X^3$, and $X^4$ containing ring. In some embodiments, the Ring A moiety is a $C_6$ cycloalkyl, such as optionally substituted by 1-5 R³ groups, wherein represents the attachment points where two adjacent carbon atoms are fused to the $X^1$, $X^2$, $X^3$, and $X^4$ containing ring. In some embodiments, the Ring A moiety is a $C_7$ cycloalkyl, such as optionally substituted by 1-5 R³ groups, wherein represents the attachment points where two adjacent carbon atoms are fused to the $X^1$, $X^2$, $X^3$, and $X^4$ containing ring. In some embodiments, the Ring A moiety is $C_6$ aryl, such as optionally substituted by 1-5 R³ groups, wherein represents the attachment points where two adjacent carbon atoms are fused to the $X^1$, $X^2$, $X^3$, and $X^4$ containing ring.

In some embodiments, each R³ is independently $C_1$-$C_6$ alkyl, —O($C_1$-$C_6$ alkyl), halo, —CN, hydroxyl, —NH₂, —NH($C_1$-$C_6$ alkyl), —N($C_1$-$C_6$ alkyl)₂, or CO₂H. In some embodiments, each R³ is independently $C_1$-$C_3$ alkyl, —O($C_1$-$C_3$ alkyl), halo, —CN, hydroxyl, —NH₂, —NH($C_1$-$C_3$ alkyl), —N($C_1$-$C_3$ alkyl)₂, or CO₂H. In some embodiments, each R³ is independently CH₃, —OCH₃, F, Cl, —CN, hydroxyl, —NH₂, —NH(CH₃), —N(CH₃)₂, or CO₂H.

In some embodiments, R³ is $C_1$-$C_6$ alkyl. In some embodiments, R³ is $C_1$-$C_3$ alkyl, such as methyl, ethyl, n-propyl, or isopropyl. In some embodiments, R³ is —CH₃.

In some embodiments, R³ is —O($C_1$-$C_6$ alkyl). In some embodiments, R³ is —O($C_1$-$C_3$ alkyl), such as —O(methyl), —O(ethyl), —O(n-propyl), or —O(isopropyl). In some embodiments, R³ is —OCH₃.

In some embodiments, R³ is halo. In some embodiments, R³ is F, Cl, or Br. In some embodiments, R³ is F or Cl.

In some embodiments, R³ is —CN. In some embodiments, R³ is hydroxyl. In some embodiments, R³ is —NH₂. In some embodiments, R³ is CO₂H.

In some embodiments, R³ is —NH($C_1$-$C_6$ alkyl). In some embodiments, R³ is —NH($C_1$-$C_3$ alkyl), such as —NH(methyl), —NH(ethyl), —NH(n-propyl), or —NH(isopropyl). In some embodiments, R³ is —NH(CH₃).

In some embodiments, R³ is —N($C_1$-$C_6$ alkyl)₂, wherein each $C_1$-$C_6$ alkyl is independently selected. In some embodiments, R³ is —N($C_1$-$C_3$ alkyl)₂, such as —N(CH₃)₂, —N(CH₂CH₃)₂, —N(CH₂CH₂CH₃)₂, —N(CH(CH₃)₂)₂, —N(CH₃)CH₂CH₃, —N(CH₃)CH₂CH₂CH₃, —N(CH₃)CH(CH₃)₂, —N(CH₂CH₃)CH₂CH₂CH₃, —N(CH₂CH₃)CH(CH₃)₂, or —N(CH₂CH₂CH₃)CH(CH₃)₂. In some embodiments, R³ is —N(CH₃)₂.

In some embodiments, the compound of formula (I), or a tautomer thereof, or a pharmaceutically acceptable salt of any of the foregoing, is a compound of formula (I-a) or (I-b):

(I-a)

(I-b)

In some embodiments, the compound of formula (I) is an agonist of THR beta. In some embodiments, the compound of formula (I) is an agonist of THR beta and is selective over THR alpha. In some embodiments, the compound of formula (I) has at least 2-fold selectivity for THR beta over THR alpha. In some embodiments, the compound of formula (I) has at least 5-fold selectivity for THR beta over THR alpha. In some embodiments, the compound of formula (I) has at least 10-fold selectivity for THR beta over THR alpha. In some embodiments, the compound of formula (I) has at least 20-fold selectivity for THR beta over THR alpha. In some embodiments, the compound of formula (I) has at least 50-fold selectivity for THR beta over THR alpha. In some embodiments, the compound of formula (I) has at least 75-fold selectivity for THR beta over THR alpha. In some embodiments, the compound of formula (I) has at least 100-fold selectivity for THR beta over THR alpha. In some embodiments, the compound of formula (I) has at least 2-, 3-, 4-, 5-, 6-, 7-, 8-, 9-, 10-, 15-, 20-, 25-, 30-, 35-, 40-, 45-, 50-, 55-, 60-, 65-, 70-, 75-, 80-, 85-, 90-, 95-, or 100-fold selectivity for THR beta over THR alpha. In any such embodiment, in one aspect selectivity is assessed via a biochemical assay, such as the TR-FRET assay described in Example B1.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to $R^1$ of formula (I) may be combined with every description, variation, embodiment or aspect of $R^2$, $R^3$, $X^1$, $X^2$, $X^3$, and $X^4$ the same as if each and every combination were specifically and individually listed. It is also understood that all descriptions, variations, embodiments or aspects of formula (I), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae as detailed herein, such as formulae (I-a) and (I-b), and are equally described, the same as if each and every description, variation, embodiment or aspect were separately and individually listed for all formulae.

In some embodiments, provided is a compound selected from the compounds in Table 1, or pharmaceutically acceptable salt thereof Although certain compounds described in the present disclosure, including in Table 1, are presented as specific stereoisomers and/or in a non-stereochemical form, it is understood that any or all stereochemical forms, including any enantiomeric or diastereomeric forms, and any tautomers or other forms of any of the compounds of the present disclosure, including in Table 1, are herein described.

In one embodiment, provided herein is a compound selected from those tabulated below in Table 1:

TABLE 1

| Example | Structure |
|---|---|
| 1 | 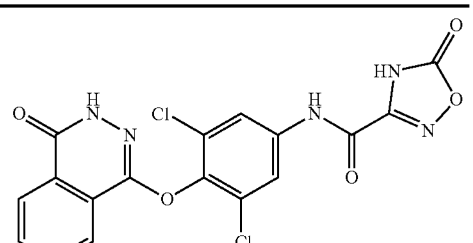 |
| 2 | | or a tautomer thereof, or a pharmaceutically acceptable salt of any of the foregoing.

In some embodiments, provided herein is a compound selected from those listed in Table 1 or a pharmaceutically acceptable salt thereof.

The invention also includes all salts, such as pharmaceutically acceptable salts, of compounds referred to herein. The invention also includes any or all of the stereochemical forms, including any enantiomeric or diastereomeric forms, and any tautomers or other forms, such as N-oxides, solvates, prodrugs, or isotopomers, of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

General Synthetic Methods

The compounds of the present disclosure may be prepared by a number of processes as generally described below and more specifically in the Examples hereinafter (such as the schemes provided in the Examples below).

The intermediates described in the following preparations may contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis* (T. Greene and P. Wuts, eds., 2d ed. 1991).

The compounds of the present invention, or salts thereof, may be prepared by a variety of procedures known in the art, some of which are illustrated in the Examples below. The specific synthetic steps for each of the routes described may be combined in different ways to prepare compounds of the invention, or salts thereof. The products of each step can be recovered by conventional methods well known in the art, including extraction, evaporation, precipitation, chromatography, filtration, trituration, and crystallization. The reagents and starting materials are readily available to one of ordinary skill in the art. Others may be made by standard techniques of organic and heterocyclic chemistry which are analogous to the syntheses of known structurally-similar compounds and the procedures described in the Examples which follow including any novel procedures.

Compounds of general formula ID can be prepared according to Scheme 1, wherein $X^1$, $X^2$, $X^3$, and $X^4$ are as defined for formula (I), or any applicable variations detailed herein, and X is halide.

27

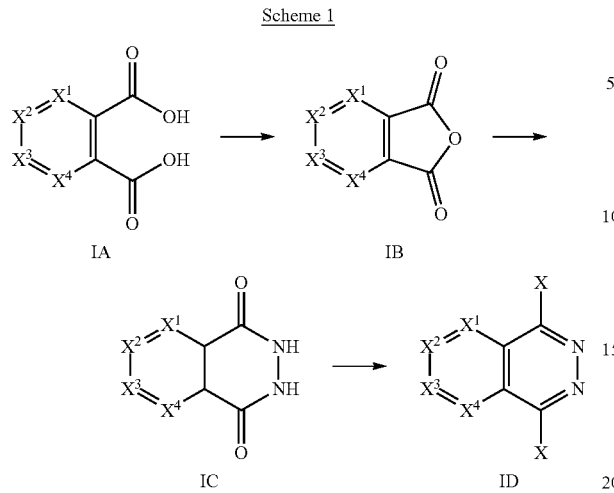

Dehydration of dicarboxylic acid of general formula IA yields cyclic anhydride of general formula IB. Cyclic anhydride of general formula IB can be transformed to hydrazine dicarbonyl of general formula IC, which is then aromatized to fused pyridazine of general formula ID.

Compounds of general formula IF can be prepared according to Scheme 2, wherein $X^1$, $X^2$, $X^3$, and $X^4$ are as defined for formula (I), or any applicable variations detailed herein, and X is halide.

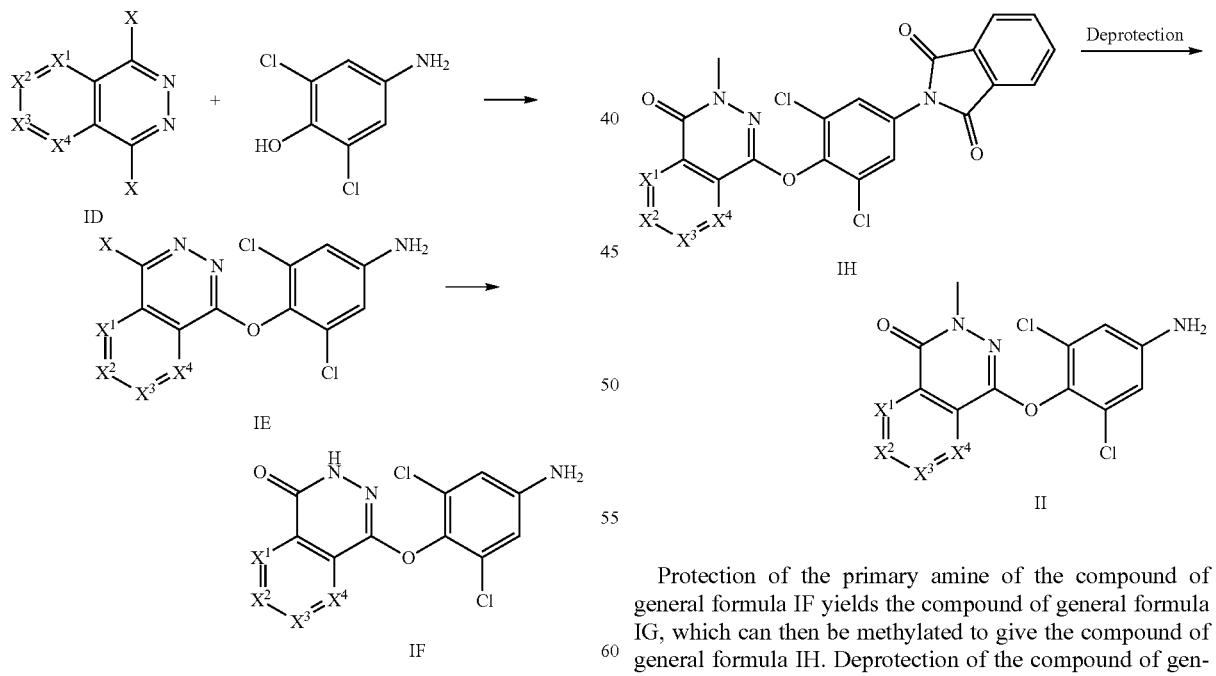

Nucleophilic aromatic substitution reaction between a compound of general formula ID and 4-amino-2,6-dichlorophenol yields a compound of general formula IE, which can then be transformed to the compound of general formula IF.

28

Compounds of general formula II can be prepared according to Scheme 3, wherein $X^1$, $X^2$, $X^3$, and $X^4$ are as defined for formula (I), or any applicable variations detailed herein.

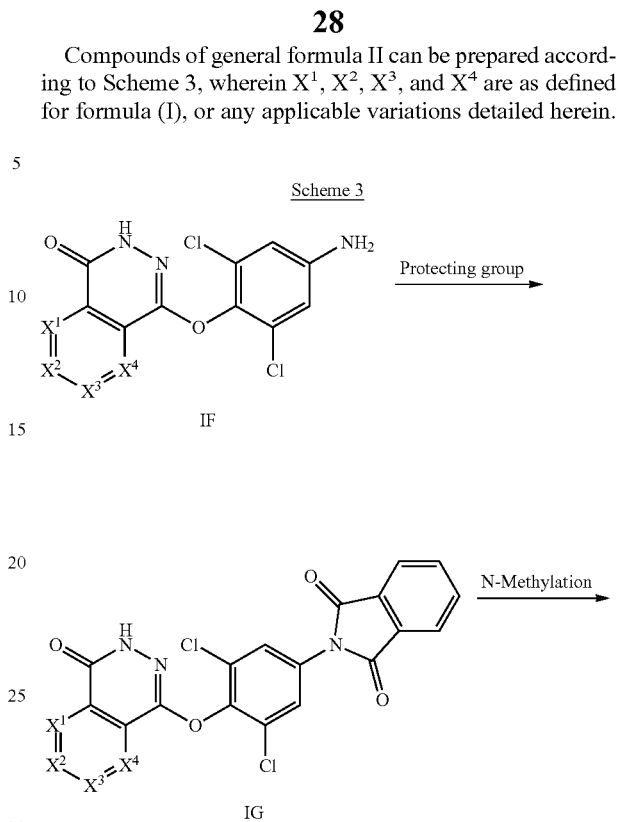

Protection of the primary amine of the compound of general formula IF yields the compound of general formula IG, which can then be methylated to give the compound of general formula IH. Deprotection of the compound of general formula IH gives the the compound of general formula II.

Compounds of formula (I) can be prepared according to Scheme 4, wherein $X^1$, $X^2$, $X^3$, and $X^4$ are as defined for formula (I), or any applicable variations detailed herein, and LG is a suitable leaving group.

Scheme 4

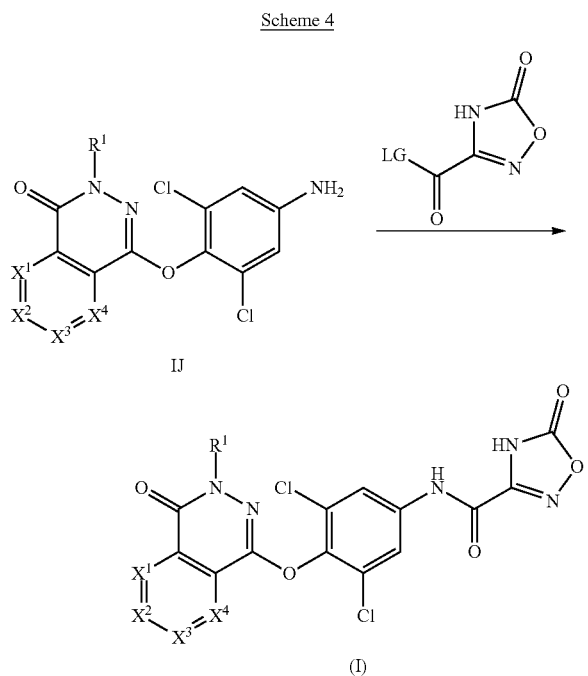

Reaction of a compound of general formula LI with a compound of general formula IK yields the compound of formula (I).

Pharmaceutical Compositions and Formulations

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound selected from a compound of Table 1 intends a composition that contains no more than 35% impurity, wherein the impurity denotes a compound other than the compound or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15%, no more than 10%, no more than 5%, no more than 3%, or no more than 1% impurity, which impurity may be the compound in a different stereochemical form. For instance, and without limitation, a composition of substantially pure (S) compound means that the composition contains no more than 15%, or no more than 10%, or no more than 5%, or no more than 3%, or no more than 1% of the (R) form of the compound.

In one variation, the compounds provided herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington: The Science and Practice of Pharmacy, Lippincott Williams & Wilkins, 21$^{st}$ ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid polyols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described.

Compositions comprising a compound, or a salt thereof, provided herein are also described. In one variation, the composition comprises a compound and a pharmaceutically acceptable carrier or excipient. In another variation, a composition of substantially pure compound, or a salt thereof, is provided.

Methods of Use/Treatments

Compounds and compositions detailed herein, such as a pharmaceutical composition containing a compound of any formula provided herein, or a pharmaceutically acceptable salt thereof, and a pharmaceutically acceptable carrier or excipient, may be used in methods of administration and treatment as provided herein. The compounds and compositions may also be used in in vitro methods, such as in vitro methods of administering a compound, or a salt thereof, or composition to cells for screening purposes and/or for conducting quality control assays.

In one aspect, provided herein is a method of agonizing thyroid hormone receptor beta (THR beta) comprising contacting either an effective amount of a compound, or a salt thereof, provided herein, or an effective amount of a pharmaceutical composition provided herein, with the THR beta.

In one aspect, provided herein is a method of treating a disorder, which is mediated by THR beta, in a patient, comprising administering to the patient in need thereof a therapeutically effective amount of a compound provided herein, or a therapeutically effective amount of a composition provided herein.

Methods of treating a disorder mediated by THR beta, including without limitation non-alcoholic fatty liver disease, non-alcoholic steatohepatitis, and symptoms and manifestations of each thereof are well known to the skilled artisan and can be adapted to treating such a disorder with a compound or composition provided herein.

In one aspect, provided herein is a method of agonizing thyroid hormone receptor beta (THR beta) comprising contacting either an effective amount of a compound provided herein, or a salt thereof, such as a pharmaceutically acceptable salt thereof, or an effective amount of a pharmaceutical composition provided herein, with the THR beta. In one aspect, provided herein is a method of selectively agonizing THR beta over THR alpha comprising contacting either an effective amount of a compound provided herein, or a pharmaceutically acceptable salt thereof, or an effective amount of a pharmaceutical composition provided herein, with the THR beta. In one such aspect, the method selectively agonizes THR beta over THR alpha by at least 2-, 3-, 4-, 5-, 6-, 7-, 8-, 9-, 10-, 15-, 20-, 25-, 30-, 35-, 40-, 45-, 50-, 55-, 60-, 65-, 70-, 75-, 80-, 85-, 90-, 95-, or 100-fold. In any such embodiment, in one aspect selectivity is assessed via a biochemical assay, such as the TR-FRET assay described in Example B1.

In one aspect, provided herein is a method of treating a disease or disorder that is mediated by THR beta in a patient in need thereof, comprising administering to the patient a therapeutically effective amount of a compound provided herein, or a pharmaceutically acceptable salt thereof, or a therapeutically effective amount of a composition provided herein. In one aspect, the disease or disorder is a liver disease or disorder. In one aspect, provided herein is a method of treating a disease or disorder of the liver associated with sub-optimal THR beta agonism in a patient in need thereof, comprising administering to the patient a compound of formula (I), or a pharmaceutically acceptable salt thereof, wherein the compound selectively agonizes THR beta over THR alpha.

In one aspect, provided herein is a method of treating non-alcoholic fatty liver disease in a patient in need thereof, comprising administering to the patient a therapeutically effective amount of a compound provided herein, or a pharmaceutically acceptable salt thereof, or a therapeutically effective amount of a composition provided herein. In one aspect, provided herein is a method of treating non-alcoholic steatohepatitis (NASH) in a patient in need thereof, comprising administering to the patient a therapeutically effective amount of a compound provided herein, or a pharmaceutically acceptable salt thereof, or a therapeutically effective amount of a composition provided herein. In one aspect, provided herein is a method of treating metabolic syndrome in a patient in need thereof, comprising administering to the patient a therapeutically effective amount of a compound provided herein, or a pharmaceutically acceptable salt thereof, or a therapeutically effective amount of a composition provided herein. In one aspect, provided herein is a method of treating dyslipidemia in a patient in need thereof, comprising administering to the patient a therapeutically effective amount of a compound provided herein, or a pharmaceutically acceptable salt thereof, or a therapeutically effective amount of a composition provided herein. In one aspect, provided herein is a method of treating hypertriglyceridemia in a patient in need thereof, comprising administering to the patient a therapeutically effective amount of a compound provided herein, or a pharmaceutically acceptable salt thereof, or a therapeutically effective amount of a composition provided herein. In one aspect, provided herein is a method of treating hypercholesterolemia in a patient in need thereof, comprising administering to the patient a therapeutically effective amount of a compound provided herein, or a pharmaceutically acceptable salt thereof, or a therapeutically effective amount of a composition provided herein.

In any of the embodiments described herein, a patient having a disease or disorder associated with THR beta agonism may include, but is not limited to, a patient with an underlying hypothyroid disorder.

In another aspect is provided a method of delaying the onset and/or development of a disease or disorder that is mediated by THR beta in a patient (such as a human) who is at risk for developing the disease or disorder. It is appreciated that delayed development may encompass prevention in the event the individual does not develop the disease or disorder. An individual at risk of developing a disease or disorder that is mediated by THR beta in one aspect has one or more risk factors for developing the disease or disorder, such as age, increased waist circumference, high body to mass index or the presence of an associated comorbidity.

In one aspect, provided herein is a method of delaying the onset and/or development of non-alcoholic fatty liver disease in a patient in need thereof, comprising administering to the patient a therapeutically effective amount of a compound provided herein, or a pharmaceutically acceptable salt thereof, or a therapeutically effective amount of a composition provided herein. In one aspect, provided herein is a method of delaying the onset and/or development of non-alcoholic steatohepatitis (NASH) in a patient in need thereof, comprising administering to the patient a therapeutically effective amount of a compound provided herein, or a pharmaceutically acceptable salt thereof, or a therapeutically effective amount of a composition provided herein. In one aspect, provided herein is a method of delaying the onset and/or development of metabolic syndrome in a patient in need thereof, comprising administering to the patient a therapeutically effective amount of a compound provided herein, or a pharmaceutically acceptable salt thereof, or a therapeutically effective amount of a composition provided herein. In one aspect, provided herein is a method of delaying the onset and/or development of dyslipidemia in a patient in need thereof, comprising administering to the patient a therapeutically effective amount of a compound provided herein, or a pharmaceutically acceptable salt thereof, or a therapeutically effective amount of a composition provided herein. In one aspect, provided herein is a method of delaying the onset and/or development of hypertriglyceridemia in a patient in need thereof, comprising administering to the patient a therapeutically effective amount of a compound provided herein, or a pharmaceutically acceptable salt thereof, or a therapeutically effective amount of a composition provided herein. In one aspect, provided herein is a method of delaying the onset and/or development of hypercholesterolemia in a patient in need thereof, comprising administering to the patient a therapeutically effective amount of a compound provided herein, or a pharmaceutically acceptable salt thereof, or a therapeutically effective amount of a composition provided herein.

In one aspect, provided herein is a compound of formula (I) or any variation thereof, or a pharmaceutically acceptable salt thereof, for use in therapy. In some embodiments, provided herein is a compound of formula (I) or any variation thereof, or a pharmaceutically acceptable salt thereof, or a pharmaceutical composition comprising such compound or a pharmaceutically acceptable salt thereof, for use in the treatment of non-alcoholic fatty liver disease. In some embodiments, provided herein is a compound of formula (I) or any variation thereof, or a pharmaceutically acceptable salt thereof or pharmaceutical composition comprising such compound, or a pharmaceutically acceptable salt thereof, for use in the treatment of non-alcoholic steatohepatitis (NASH). In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of metabolic syndrome. In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of dyslipidemia. In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of hypertriglyceridemia. In some embodiments, provided is a compound of formula (I) or any variation thereof, or a pharmaceutically acceptable salt thereof, or a pharmaceutical composition comprising such compound or a pharmaceutically acceptable salt thereof, for use in the treatment of hypercholesterolemia.

In another embodiment, provided herein is a compound of formula (I) or any variation thereof, or a pharmaceutically acceptable salt thereof, for use in the manufacture of a medicament for the treatment of non-alcoholic fatty liver disease. In another embodiment, provided herein is a compound of formula (I) or any variation thereof, or a pharmaceutically acceptable salt thereof, for use in the manufacture of a medicament for the treatment of non-alcoholic steatohepatitis (NASH). In another embodiment, provided herein is a compound of formula (I) or any variation thereof, or a pharmaceutically acceptable salt thereof, for use in the manufacture of a medicament for the treatment of metabolic syndrome. In some embodiments, the medicament is for the treatment of dyslipidemia. In some embodiments, the medicament is for the treatment of hypertriglyceridemia. In some embodiments, the medicament is for the treatment of dyslipidemia. In some embodiments, the medicament is for the treatment of hypercholesterolemia.

In some embodiments, the individual is a mammal. In some embodiments, the individual is a primate, dog, cat, rabbit, or rodent. In some embodiments, the individual is a primate. In some embodiments, the individual is a human. In some embodiments, the human is at least about or is about any of 18, 21, 30, 50, 60, 65, 70, 75, 80, or 85 years old. In some embodiments, the human is a child. In some embodiments, the human is less than about or about any of 21, 18, 15, 10, 5, 4, 3, 2, or 1 years old.

Dosing and Method of Administration

The dose of a compound described herein, or a stereoisomer, tautomer, solvate, or salt thereof, administered to an individual (such as a human) may vary with the particular compound or salt thereof, the method of administration, and the particular disease or disorder, such as non-alcoholic fatty liver disease, non-alcoholic steatohepatitis (NASH), metabolic syndrome, hypertriglyceridemia, dyslipidemia, or hypercholesterolemia, being treated. In some embodiments, the amount of the compound, or a stereoisomer, tautomer, solvate, or salt thereof, is a therapeutically effective amount.

The compounds provided herein, or a salt thereof, may be administered to an individual via various routes, including, e.g., intravenous, intramuscular, subcutaneous, oral, and transdermal.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein, or a stereoisomer, tautomer, solvate, or salt thereof, and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Articles of Manufacture and Kits

The present disclosure further provides articles of manufacture comprising a compound described herein, or a salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein, or a pharmaceutically acceptable salt thereof, or a composition comprising a compound described herein, or a pharmaceutically acceptable salt thereof. The kits may employ any of the compounds disclosed herein or a pharmaceutically acceptable salt thereof. In one variation, the kit employs a compound described herein or a pharmaceutically acceptable salt thereof. The kits may be used for any one or more of the uses described herein, and, accordingly, may contain instructions for the treatment of any disease or described herein, for example for the treatment of non-alcoholic steatohepatitis (NASH).

Kits generally comprise suitable packaging. The kits may comprise one or more containers comprising any compound described herein or a pharmaceutically acceptable salt thereof. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein, or a pharmaceutically acceptable salt thereof, and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

EXAMPLES

It is understood that the present disclosure has been made only by way of example, and that numerous changes in the combination and arrangement of parts can be resorted to by those skilled in the art without departing from the spirit and scope of present disclosure.

The chemical reactions in the Examples described can be readily adapted to prepare a number of other compounds disclosed herein, and alternative methods for preparing the compounds of this disclosure are deemed to be within the scope of this disclosure. For example, the synthesis of non-exemplified compounds according to the present disclosure can be successfully performed by modifications apparent to those skilled in the art, e.g., by appropriately protecting interfering groups, by utilizing other suitable reagents known in the art other than those described, or by making routine modifications of reaction conditions, reagents, and starting materials. Alternatively, other reactions disclosed herein or known in the art will be recognized as having applicability for preparing other compounds of the present disclosure.

Abbreviations used in the Examples include the following:

Ac: acetyl
DMF: dimethylformamide
DMF-DMA: dimethylformamide dimethylacetal
DMSO: dimethyl sulfoxide
EtOAc: ethyl acetate
FA: formic acid
$^1$H NMR: proton nuclear magnetic resonance
HPLC: high-performance liquid chromatography
LCMS: liquid chromatography-mass spectrometry
MeCN: acetonitrile
MeOH: methanol or methyl alcohol
TEA: triethylamine
THF: tetrahydrofuran
TLC: thin-layer chromatography Synthetic Examples Example S1

Synthesis of N-(3,5-dichloro-4-((4-oxo-3,4-dihydrophthalazin-1-yl)oxy)phenyl)-5-oxo-4,5-dihydro-1,2,4-oxadiazole-3-carboxamide

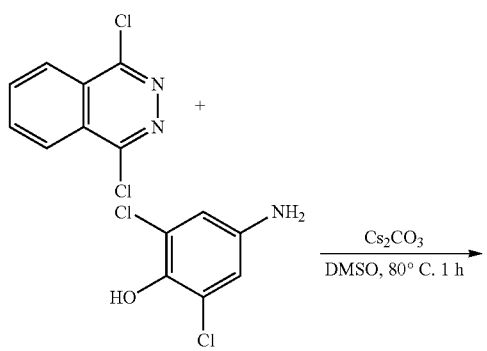

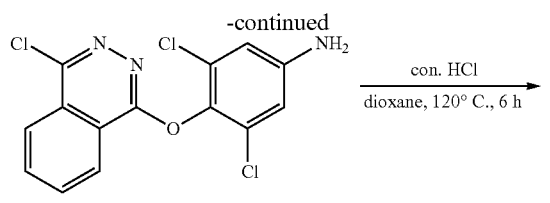

1a

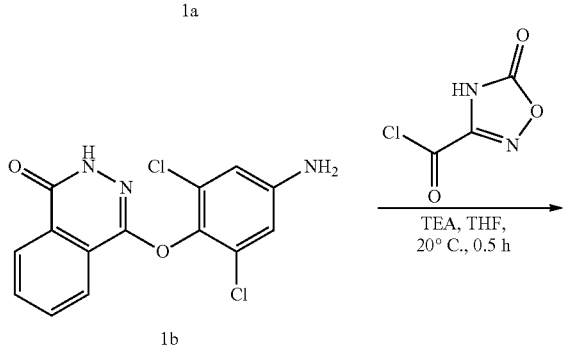

1b

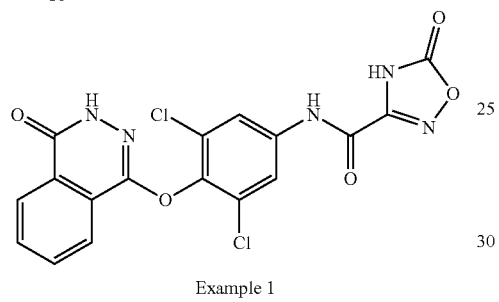

Example 1

Synthesis of 3,5-dichloro-4-((4-chlorophthalazin-1-yl)oxy)aniline (1a). To a solution of 1,4-dichlorophthalazine (100 g, 502.4 mmol) and 4-amino-2,6-dichlorophenol (107.3 g, 602.9 mmol) in DMSO (1.0 L) was added $Cs_2CO_3$ (196.4 g, 602.9 mmol). Then the mixture was stirred at 80° C. for 1 hour. TLC and LCMS showed the reaction was completed. The mixture cooled to 20° C., and added in HCl solution (2 M, 7.5 L). Then the mixture was filtered to collect the solid. The solid was washed with $H_2O$ (800 mL*3), and dried over in vacuum to give 1a. MS mass calculated for $[M+1]^+$ ($C_{14}H_8Cl_3N_3O$) requires m/z 340.0, LCMS found m/z 340.0; $^1$H NMR (400 MHz, DMSO-$d_6$) δ8.46-8.55 (m, 1H), 8.30-8.35 (m, 1H), 8.20-8.29 (m, 2H), 6.78 (s, 2H).

Synthesis of 4-(4-amino-2,6-dichloro-phenoxy)-2H-phthalazin-1-one (1b). To a mixture of 3,5-dichloro-4-((4-chlorophthalazin-1-yl)oxy)aniline (1a) (130 g, 381.7 mmol) in HCl (750 mL) was added dioxane (750 mL). Then the mixture was stirred at 120° C. for 3 hours. LCMS and TLC showed the reaction was completed. The reaction was cooled to 20° C. Then EtOAc was added in the combined mixture and the resulting mixture was stirred at 20° C. for 1 hour. The mixture was filtered to collect the solid. The solid was washed with $H_2O$ (500 mL*5) and dried over in vacuum to give 1b. MS mass calculated for $[M+1]^+$ ($C_{14}H_9Cl_2N_3O_2$) requires m/z 322.0, LCMS found m/z 322.0; $^1$H NMR (400 MHz, DMSO-$d_6$) δ11.95 (s, 1H), 8.15-8.34 (m, 2H), 7.89-8.09 (m, 2H), 6.76 (br s, 2H).

Synthesis of N-(3,5-dichloro-4-((4-oxo-3,4-dihydrophthalazin-1-yl)oxy)phenyl)-5-oxo-4,5-dihydro-1,2,4-oxadiazole-3-carboxamide (Example 1). To a solution of 5-oxo-4H-1,2,4-oxadiazole-3-carbonyl chloride (1.38 g, 9.31 mmol) in THF (10 mL) was added drop-wise a solution of TEA (3.14 g, 31.0 mmol, 4.32 mL) and 4-(4-amino-2,6-dichloro-phenoxy)-2H-phthalazin-1-one (1b) (2 g, 6.21 mmol) in THF (10 mL) at 20° C. over 2 hours. After addition, the mixture was stirred at this temperature for 30 minutes. TLC showed 1b were consumed completely. LCMS showed one main peak with desired MS. The mixture was diluted with $H_2O$ (50 mL) and extracted with EtOAc 30 mL (15 mL*2). The combined organic layers were washed with brine 20 mL (10 mL*2), dried over anhydrous $Na_2SO_4$, filtered to give a black brown liquid. The black brown liquid was concentrated under reduced pressure to remove solvent until a solid appeared. The mixture was stirred at 20° C. for 1 hour and filtered to give Example 1. MS mass calculated for $[M+1]^+$ ($C_{17}H_9Cl_2N_5O_5$) requires m/z 434.0, LCMS found m/z 434.0; 1H NMR (400 MHz, DMSO-$d_6$) δ12.01 (s, 1H), 11.35 (s, 1H), 8.31 (d, J=8.2 Hz, 1H), 8.24 (d, J=7.6 Hz, 1H), 8.11-8.05 (m, 1H), 8.05-7.98 (m, 3H).

Example S2

Synthesis of N-(3,5-dichloro-4-((3-methyl-4-oxo-3,4-dihydrophthalazin-1-yl)oxy)phenyl)-5-oxo-4,5-dihydro-1,2,4-oxadiazole-3-carboxamide

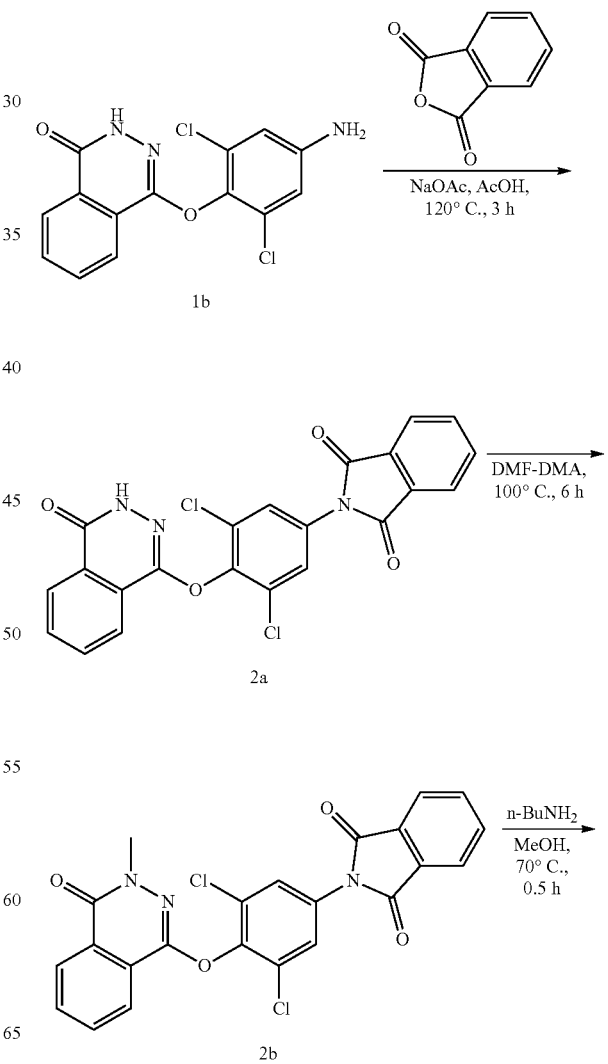

-continued

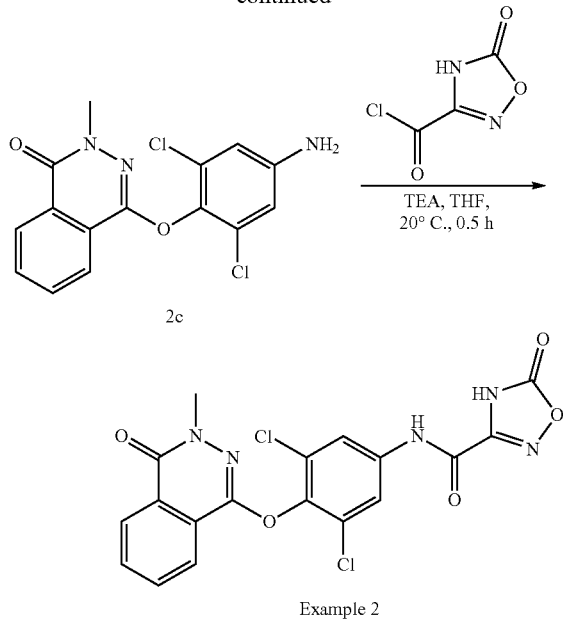

Example 2

Synthesis of 2-(3,5-dichloro-4-((4-oxo-3,4-dihydrophthalazin-1-yl)oxy)phenyl)isoindoline-1,3-dione (2a). To a solution of 4-(4-amino-2,6-dichloro-phenoxy)-2H-phthalazin-1-one (1b) (500 mg, 1.55 mmol) in AcOH (10 mL) was added isobenzofuran-1,3-dione (252.88 mg, 1.71 mmol). The mixture was stirred at 120° C. for 3 hours. TLC and LCMS showed the reaction was complete. The reaction mixture was diluted with water (30 mL) and filtered to give the pad cake. The pad cake was dried under reduced pressure to give crude 2a. The crude product was used directly in next step. MS mass calculated for [M+1]$^+$ ($C_{22}H_{11}Cl_2N_3O_4$) requires m/z 452.0, LCMS found m/z 452.0; $^1$H NMR (400 MHz, DMSO-d$_6$) δ12.06-12.03 (m, 1H), 8.36-8.25 (m, 3H), 8.14-8.09 (m, 1H), 8.07-8.02 (m, 3H), 7.99-7.94 (m, 2H), 7.85-7.85 (m, 1H).

Synthesis of 2-(3,5-dichloro-4-((3-methyl-4-oxo-3,4-dihydrophthalazin-1-yl)oxy)phenyl)isoindoline-1,3-dione (2b). A solution of 2-(3,5-dichloro-4-((4-oxo-3,4-dihydrophthalazin-1-yl)oxy)phenyl)isoindoline-1,3-dione (2a) (709 mg, 1.57 mmol) in DMF-DMA (10 mL) was stirred at 100° C. for 6 hours. LCMS showed desired m/z. The reaction mixture was diluted with water (30 mL) and filtered to give the pad cake. The pad cake was dried under reduced pressure to give crude 2b. The crude product was used directly in next step. MS mass calculated for [M+1]$^+$ ($C_{23}H_{13}Cl_2N_3O_4$) requires m/z 466.0, LCMS found m/z 466.0.

Synthesis of 4-(4-amino-2,6-dichlorophenoxy)-2-methylphthalazin-1(2H),-one (2c). To a solution of 2-(3,5-dichloro-4-((3-methyl-4-oxo-3,4-dihydrophthalazin-1-yl)oxy)phenyl)isoindoline-1,3-dione (2b) (596 mg, 1.28 mmol) in MeOH (5 mL) was added butan-1-amine (280.5 mg, 3.83 mmol, 379.0 uL). The mixture was stirred at 70° C. for 0.5 hours. The reaction mixture was diluted by H$_2$O (15 mL) at 25° C. and extracted with EtOAc (15 mL*2). The combined organic layers were washed with brine (10 mL), dried over anhydrous Na$_2$SO$_4$, filtered and concentrated under reduced pressure to give a residue. The residue was purified by prep-TLC (SiO$_2$, petroleum ether: ethyl acetate) to give 2c. MS mass calculated for [M+1]$^+$ ($C_{15}H_{11}Cl_2N_3O_2$) requires m/z 336.0, LCMS found m/z 336.0; $^1$H NMR (400 MHz, DMSO-d$_6$) δ8.33-8.2 9 (m, 1H), 8.21-8.17 (m, 1H), 8.07-7.96 (m, 2H), 6.72-6.70 (m, 2H), 5.68-5.66 (m, 2H), 3.48-3.44 (m, 3H).

Synthesis of N-(3,5-dichloro-4-((3-methyl-4-oxo-3,4-dihydrophthalazin-1-yl)oxy)phenyl)-5-oxo-4,5-dihydro-1,2,4-oxadiazole-3-carboxamide (Example 2). To a solution of 4-(4-amino-2,6-dichlorophenoxy)-2-methylphthalazin-1(2H),-one (2c) (30 mg, 89.2 umol) in THF (5 mL) was added TEA (27.1 mg, 267.7 umol, 37.3 uL) and 5-oxo-4,5-dihydro-1,2,4-oxadiazole-3-carbonyl chloride (19.9 mg, 133.9 umol). The mixture was stirred at 20 ° C. for 0.5 hours. TLC (petroleum ether: ethyl acetate: AcOH) and LC-MS showed a completed reaction. The reaction mixture was quenched by addition H$_2$O (15mL) at 25 ° C. and extracted with EtOAc (15 mL*2). The combined organic layers were dried over Na$_2$SO$_4$, filtered and concentrated under reduced pressure to give a residue. The residue was purified by prep-HPLC (column: Phenomenex Luna C18 200*40 mm*10 um; mobile phase: [water (0.2%FA)-MeCN]) to give Example 2. MS mass calculated for [M+1]$^+$ ($C_{18}H_{11}Cl_2N_5O_5$) requires m/z 448.0, LCMS found m/z 448.0; $^1$H NMR (400 MHz, DMSO-d$_6$) δ11.30 (br s, 1H), 8.35-8.31 (m, 1H), 8.24 (br d, J=7.5 Hz, 1H), 8.06 (s, 4H), 3.45 (s, 3H).

Biological Example: Biological Screening

Example B1

Time-Resolved Fluorescence Resonance Energy Transfer (TR-FRET) Assay for Thyroid Hormone Receptor Agonist Screening LanthaScreen™ TR-FRET Thyroid Receptor alpha Coactivator Assay kit (ThermoFisher) and LanthaScreen™ TR-FRET Thyroid Receptor beta Coactivator Assay kit (ThermoFisher) were used for agonist compound screening. Compounds in DMSO were diluted using ECHO Liquid Handler (Labcyte Inc.) into 384 plates in 10-point 3-fold series in duplicate (5 micro M final top concentration). Buffer C (ThermoFisher) was added to each well before the 4×mixture of fluorescein-SCR2-2 coactivator (200 nM final concentration), Terbium-labeled anti-GST antibody (2 nM final concentration), and TR alpha-LBD (0.4 nM final concentration) or TR beta-LBD (1.0 nM final concentration) was added. After 2 hour incubation at room temperature in dark, the TR-FRET signal was measured on an EnVision plate reader (PerkinElmer) with excitation at 340 nm and dual emission readout at 495 and 520 nm with the delay time of 100 micro second and the integration time of 200 micro second. The ratio of emission signal at 520 and at 495 was used to calculate $EC_{50}$ using GraphPad Prism (GraphPad Software). In every batch of compound screening, T3 (L-3, 3',5-Triiodothyronine sodium salt, >95%) (Calbiochem) was used as reference compound. The $EC_{50}$ of T3 measured were within 3-fold of the reference value provided by the assay kit manufacturer (ThermoFisher Scientific). The Z' factors measured in every batch of screening using T3 as high percent effect (HPE) control and 0.5% DMSO as zero percent effect (ZPE) control were in the range of 0.5 to 0.8. Compounds' THR-beta selectivity values are derived from T3-selectivity normalized data. Data obtained using the TR-FRET assay for certain compounds disclosed herein are listed in Table 2.

TABLE 2

| Example | EC$_{50}$ THRβ-FRET [nM] $^a$ | EC$_{50}$ THRα-FRET [nM] $^a$ | THRβ-Selectivity |
|---|---|---|---|
| 1 | 33.7 | 492.2 | 57.5 |
| 2 | 5.5 | 40.5 | 10.9 |

$^a$ all compounds were run in duplicate multiple times, and the average data is reported All publications, including patents, patent applications, and scientific articles, mentioned in this specification are herein incorporated by reference in their entirety for all purposes to the same extent as if each individual publication, including patent, patent application, or scientific article, were specifically and individually indicated to be incorporated by reference.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

The invention claimed is:

1. A compound of formula (I):

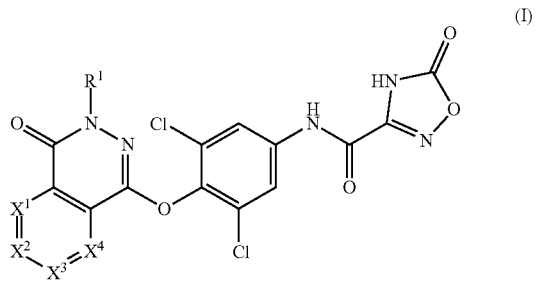

or a tautomer thereof, or a pharmaceutically acceptable salt of any of the foregoing, wherein:
$R^1$ is H or —CH$_3$;
$X^1$ $X^2$ $X^3$, and $X^4$ are each independently CR$^2$ or N, wherein at least two of $X^1$, $X^2$, $X^3$, and $X^4$ are CR$^2$;
each R$^2$ is independently H, halo, C$_1$-C$_6$ alkyl, C$_1$-C$_6$ alkyl-CN, C$_1$-C$_6$ alkyl-OH, C$_1$-C$_6$ haloalkyl, —CN, hydroxyl, —NH$_2$, —NH(C$_1$-C$_6$ alkyl), —N(C$_1$-C$_6$ alkyl)$_2$, —O(C$_1$-C$_6$ alkyl), C$_3$-C$_6$ cycloalkyl, 5- to 6-membered heteroaryl, 5- to 7-membered heterocyclyl, or C$_6$ aryl,
wherein each C$_1$-C$_6$ alkyl, —O(C$_1$-C$_6$ alkyl), C$_3$-C$_6$ cycloalkyl, 5- to 6-membered heteroaryl, 5- to 7-membered heterocyclyl, or C$_6$ aryl is optionally substituted by 1-5 R$^3$ groups;
or two R$^2$ groups are taken together with the carbon atoms to which they are attached to form a 5- to 6-membered heteroaryl, 5- to 7-membered heterocyclyl, C$_5$-C$_7$ cycloalkyl, or C$_6$ aryl, each of which is optionally substituted by 1-5 R$^3$ groups; and
each R$^3$ is independently C$_1$-C$_6$ alkyl, —O(C$_1$-C$_6$ alkyl), halo, —CN, hydroxyl, —NH$_2$, —NH(C$_1$-C$_6$ alkyl), —N(C$_1$-C$_6$ alkyl)$_2$, or CO$_2$H.

2. The compound of claim 1, or a tautomer thereof, or a pharmaceutically acceptable salt of any of the foregoing, wherein:
$R^1$ is H.

3. The compound of claim 1, or a tautomer thereof, or a pharmaceutically acceptable salt of any of the foregoing, wherein:
$R^1$ is —CH$_3$.

4. The compound of claim 1, or a tautomer thereof, or a pharmaceutically acceptable salt of any of the foregoing, wherein:
$X^1$, $X^2$, $X^3$, and $X^4$ are each independently CR$^2$.

5. The compound of claim 1, or a tautomer thereof, or a pharmaceutically acceptable salt of any of the foregoing, wherein:
one of $X^1$, $X^2$, $X^3$, and $X^4$ is N.

6. The compound of claim 1, or a tautomer thereof, or a pharmaceutically acceptable salt of any of the foregoing, wherein:
two of $X^1$, $X^2$, $X^3$, and $X^4$ are N.

7. The compound of claim 1, or a tautomer thereof, or a pharmaceutically acceptable salt of any of the foregoing, wherein:
each R$^2$ is independently H, halo, C$_1$-C$_3$ alkyl, C$_1$-C$_3$ alkyl-CN, C$_1$-C$_3$ alkyl-OH, C$_1$-C$_3$ haloalkyl, —CN, hydroxyl, —NH$_2$, —NH(C$_1$-C$_3$ alkyl), —N(C$_1$-C$_3$ alkyl)$_2$, —O(C$_1$-C$_3$ alkyl), C$_3$-C$_6$ cycloalkyl, 5- to 6-membered heteroaryl, 5- to 6-membered heterocyclyl, or C$_6$ aryl,
wherein each C$_1$-C$_3$ alkyl, —O(C$_1$-C$_3$ alkyl), C$_3$-C$_6$ cycloalkyl, 5- to 6-membered heteroaryl, 5- to 6-membered heterocyclyl, or C$_6$ aryl is optionally substituted by 1-5 R$^3$ groups.

8. The compound of claim 7, or a tautomer thereof, or a pharmaceutically acceptable salt of any of the foregoing, wherein:
each R$^2$ is independently H, halo, or C$_1$-C$_3$ alkyl optionally substituted by 1-2 R$^3$ groups.

9. The compound of claim 8, or a tautomer thereof, or a pharmaceutically acceptable salt of any of the foregoing, wherein:
each R$^2$ is independently H, F, Cl, or —CH$_3$.

10. The compound of claim 9, or a tautomer thereof, or a pharmaceutically acceptable salt of any of the foregoing, wherein:
each R$^2$ is H.

11. The compound of claim 1, or a tautomer thereof, or a pharmaceutically acceptable salt of any of the foregoing, wherein:
one or two of R$^2$ are independently selected from the group consisting of halo, C$_1$-C$_3$ alkyl, C$_1$-C$_3$ alkyl-CN, C$_1$-C$_3$ alkyl-OH, C$_1$-C$_6$ haloalkyl, —CN, hydroxyl, —NH$_2$, —NH(C$_1$-C$_3$ alkyl), —N(C$_1$-C$_3$ alkyl)$_2$, —O(C$_1$-C$_3$ alkyl), C$_3$-C$_6$ cycloalkyl, 5- to 6-membered heteroaryl, 5- to 6-membered heterocyclyl, and C$_6$ aryl,
wherein each C$_1$-C$_3$ alkyl, —O(C$_1$-C$_3$ alkyl), C$_3$-C$_6$ cycloalkyl, 5- to 6-membered heteroaryl, 5- to 6-membered heterocyclyl, and C$_6$ aryl,
wherein each C$_1$-C$_3$ alkyl, —O(C$_1$-C$_3$ alkyl), C$_3$-C$_6$ cycloalkyl, 5- to 6-membered heteroaryl, 5- to 6-membered heterocyclyl, or C$_6$ aryl is optionally substituted by 1-5 R$^3$ groups.

12. The compound of claim 1, or a tautomer thereof, or a pharmaceutically acceptable salt of any of the foregoing, wherein:
two R$^2$ groups are taken together with the carbon atoms to which they are attached to form a 5- to 6-membered heteroaryl, 5- to 6-membered heterocyclyl, C$_5$-C$_6$ cycloalkyl, or C$_6$ aryl, each of which is optionally substituted by 1-5 R$^3$ groups.

13. The compound of claim 1, or a tautomer thereof, or a pharmaceutically acceptable salt of any of the foregoing, wherein:

each $R^3$, if present, is independently $C_1$-$C_3$ alkyl, —O($C_1$-$C_3$ alkyl), halo, —CN, hydroxyl, —NH$_2$, —NH($C_1$-$C_3$ alkyl), —N($C_1$-$C_3$ alkyl)$_2$, or CO$_2$H.

14. The compound of claim 13, or a tautomer thereof, or a pharmaceutically acceptable salt of any of the foregoing, wherein:

each $R^3$ is independently CH$_3$, —OCH$_3$, F, Cl, —CN, hydroxyl, —NH$_2$, —NH(CH$_3$), —N(CH$_3$)$_2$, or CO$_2$H.

15. The compound of claim 1, which is:

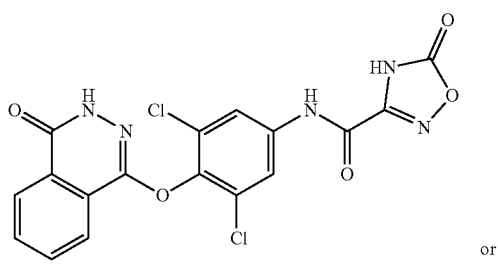

or

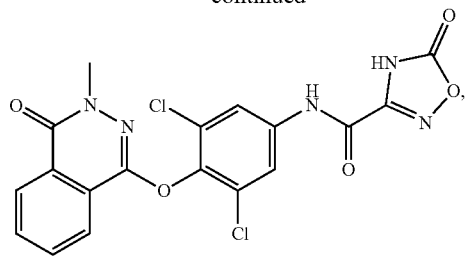

or a tautomer thereof, or a pharmaceutically acceptable salt of any of the foregoing.

16. A pharmaceutical composition comprising the compound of claim 1, or a tautomer thereof, or a pharmaceutically acceptable salt of any of the foregoing, and at least one pharmaceutically acceptable excipient.

17. A method of agonizing thyroid hormone receptor beta (THR beta) comprising contacting either an effective amount of the compound of claim 1, or a tautomer thereof, or a pharmaceutically acceptable salt of any of the foregoing.

18. A method of treating a disorder which is mediated by THR beta in a patient in need thereof, comprising administering to the patient a effective amount of the compound of claim 1, or a tautomer thereof, or a pharmaceutically acceptable salt of any of the foregoing.

19. The method of claim 18, wherein the disorder is non-alcoholic steatohepatitis (NASH).

* * * * *